United States Patent
Weber et al.

(10) Patent No.: US 11,161,812 B2
(45) Date of Patent: *Nov. 2, 2021

(54) PRODUCTION OF CYCLIC IMIDES SUITABLE FOR OXIDATION CATALYSIS

(71) Applicant: ExxonMobil Chemical Patents Inc., Baytown, TX (US)

(72) Inventors: Jörg F. W. Weber, Houston, TX (US); Helge Jaensch, Grimbergen (BE); Andrew R. Witt, Huffman, TX (US); Christopher L. Becker, Manhattan, KS (US); Kirk C. Nadler, Houston, TX (US); Kendele S. Galvan, Houston, TX (US); Amy B. Batton, Baytown, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/096,091

(22) PCT Filed: Apr. 18, 2017

(86) PCT No.: PCT/US2017/028027
§ 371 (c)(1),
(2) Date: Oct. 24, 2018

(87) PCT Pub. No.: WO2017/204935
PCT Pub. Date: Nov. 30, 2017

(65) Prior Publication Data
US 2019/0135749 A1 May 9, 2019

Related U.S. Application Data

(60) Provisional application No. 62/341,971, filed on May 26, 2016.

(51) Int. Cl.
*B01J 19/00* (2006.01)
*B01J 19/18* (2006.01)
*C07D 209/48* (2006.01)
*C07D 307/89* (2006.01)

(52) U.S. Cl.
CPC ........ *C07D 209/48* (2013.01); *B01J 19/0013* (2013.01); *B01J 19/0066* (2013.01); *B01J 19/18* (2013.01); *B01J 2219/00029* (2013.01); *B01J 2219/00051* (2013.01); *B01J 2219/00164* (2013.01); *C07D 307/89* (2013.01)

(58) Field of Classification Search
CPC combination set(s) only.
See application file for complete search history.

(56) References Cited

U.S. PATENT DOCUMENTS

| 3,351,426 A | 11/1967 | Leaver et al. |
| 4,954,639 A | 9/1990 | Fertel et al. |
| 4,956,168 A | 9/1990 | Wagaman |
| 5,472,679 A | 12/1995 | Levinthal et al. |
| 6,299,734 B1 | 10/2001 | Watzenberger et al. |
| 6,316,639 B1 | 11/2001 | Fritz-Langhals |
| 7,368,615 B2 | 5/2008 | Ishii et al. |
| 7,396,519 B2 | 7/2008 | Lin et al. |
| 7,582,774 B2 | 9/2009 | Kajikawa et al. |
| 8,658,804 B2 | 2/2014 | Jaensch et al. |
| 2002/0169331 A1* | 11/2002 | Miura .................... C07C 51/313 552/1 |
| 2006/0229196 A1* | 10/2006 | Ishii ........................ C07C 45/36 502/162 |
| 2006/0281629 A1 | 12/2006 | Ishii et al. |
| 2013/0203984 A1 | 8/2013 | Becker et al. |

(Continued)

FOREIGN PATENT DOCUMENTS

| CN | 1051170 | 5/1991 |
| CN | 101845012 | 9/2010 |
| DE | 130 681 C | 4/1902 |

(Continued)

OTHER PUBLICATIONS

Khan, "Effect of Hydroxylamine Buffers on Apparent Equilibrium Constant for Reversible Conversion of N-Hydroxyphthalimide to o-(N-Hydroxycarbamoyl)-Benzohydroxamic Acid: Evidence for Occurrence of General Acid-Base Catalysis," Indian Journal of Chemistry, 1991, vol. 30A, pp. 777-783.

Jianguo, "A Facile Synthesis of N-hydroxyphthalimide" Guangdong Chemical Industry, 2012, vol. 39, No. 4, pp. 49-50.

L. Bauer et al., "The Chemistry of Hydroxamic Acids and N-Hydroxyimides," Angewandte Chemie, International Edition, vol. 13, No. 6, pp. 376-384, 1974.

W. R. Roderick et al., "Colorless and Yellow Forms of N-Hydroxyphthalimide," Journal of the Amercian Chemical Society, vol. 79, No. 19, pp. 5196-5198, 1957.

(Continued)

*Primary Examiner* — Amanda L. Aguirre

(57) ABSTRACT

Disclosed are novel processes for the production of cyclic imide compounds such as N-hydroxyphthalimide (NHPI). The processes may be particularly well-suited for commercial-scale production of cyclic imides such as NHPI. Such cyclic imide compounds are suitable for use as oxidation catalysts, and specifically may be used to oxidize cyclohexylbenzene to cyclohexyl-1-phenyl-1-hydroperoxide. Such an oxidation may be particularly useful in a process for the production of phenol and/or cyclohexanone from benzene via a process comprising hydroalkylation of benzene to cyclohexylbenzene, oxidation of the cyclohexylbenzene to cyclohexyl-1-phenyl-1-hydroperoxide, and cleavage of the cyclohexyl-1-phenyl-1-hydroperoxide to phenol and cyclohexanone. The cyclic imide production process may advantageously include water washing and reactant recovery steps to maximize purity and yield.

18 Claims, 3 Drawing Sheets

(56) References Cited

U.S. PATENT DOCUMENTS

| | | | |
|---|---|---|---|
| 2013/0211036 A1 | 8/2013 | Dakka et al. | |
| 2014/0148569 A1 | 5/2014 | Dakka et al. | |

FOREIGN PATENT DOCUMENTS

| | | | |
|---|---|---|---|
| DE | 1247282 | 8/1967 | |
| DE | 3528463 | 2/1987 | |
| DE | 3601803 | 7/1987 | |
| EP | 108294 | 5/1984 | |
| JP | 2001-233854 | 8/2001 | |
| JP | 2002-047270 | 2/2002 | |
| JP | 2002-128760 | 5/2002 | |
| JP | 2003-081941 | 3/2003 | |
| JP | 2004-051626 | 2/2004 | |
| WO | WO 95/25090 | 9/1995 | |
| WO | WO 97/22551 | 6/1997 | |
| WO | WO-2010120398 A2 * | 10/2010 | ........... C07D 209/48 |
| WO | WO 2014/137623 | 9/2014 | |
| WO | WO 2016/053583 | 4/2016 | |
| WO | 2017/204936 A1 | 4/2017 | |

OTHER PUBLICATIONS

H. Reichelt, C. A, Faunce and H. H. Paradies, "Elusive Forms and Structures of N-Hydroxyphthalimide: The Colorless and Yellow Crystal Forms of N-Hydroxyphthalimide," J. Phys. Chem. A, vol. 111, pp. 2587-2601, 2007.

M. S. Mannan, "Thermal decomposition pathways of hydroxylamine: Theoretical Investigation on the Initial Steps," J. Phys. Chem. A, vol. 114, pp. 9262-9269, 2010.

Y. Iwata, "Study on decomposition of hydroxylamine/water solution," Journal of Loss Prevention in Process Industries, vol. 16, pp. 41-53, 2003.

Y. Iwata, "Decomposition of hydroxylamine/water solution with added iron," Journal of Hazardous Materials, vol. 104, pp. 39-49, 2003.

A. Sakakura, R. Yamashita, T. Ohkubo, M. Akakura and K. Ishihara, "Intramolecular Dehydrative Condensation of Dicarboxylic Acids with Bronsted Base-Assisted Boronic Acid Catalysts," Australian Journal of Chemistry, vol. 64, No. 11, pp. 1458-1465, 2011.

Agrawal, "Dissociation Constants of Some Hydroxamic Acids," Zeitschrift fuer Naturforschung, 1976, vol. 31B, No. 5, pp. 605-606.

Benjamin et al., "The Synthesis of Unsubstituted Cyclic Imides Using Hydroylamine Under Microwave Irradiation," Molecules, 2008, vol. 13, pp. 157-169.

Edafiogho et al., "Synthesis and Anticonvulsant Activity of Imidooxy Derivatives ," Journal of Med. Chemistry, 1991, vol. 34, pp. 387-392.

Einhorn et al,, "Mild and Convenient One Pot Synthesis of N-Hydroxyimides from N-Unsubstituted Imides," Synthetic Communications, 2001, vol. 31, No. 5, pp. 741-748.

Gross et al., "Zur Darstellung Von N-Hydroxyphthalimid Und N-Hydroxysuccinimid," Journal fur praktische Chemie, 1969, vol. 311, pp. 692-693.

Imai et al., "The Reaction of N-(Mesyloxy)Phthalimide and N-(Mesyloxy)Succinimide With Various Amines," Nippon Kagaku Kaishi, 1975, vol. 12, pp. 2154-2160 (English Abstract).

Karakurt et al., "Synthesis of Some 1-(2-Napthyl)-2-(Imidazole-1-yl) Ethanone Oxime and Oxime Ether Derivatives and Their Anticonvulsant and Antimicrobial Activities," European Journal of Medical Chemistry, 2001, vol. 36, pp. 421-433.

Sugamoto et al., "Microwave-Assisted Synthesis of N-Hydroxyphthalimide Derivatives," Synthetic Communications, 2005, vol. 35, pp. 67-70.

M. S. Mannan, "Reaction pathways of hydroxylamine decomposition in the presence of acid/base," ISBN: 0-8169-0965-2, AIChE Annual Meeting in Austin, Texas, (2004).

* cited by examiner

PRODUCTION OF CYCLIC IMIDES SUITABLE FOR OXIDATION CATALYSIS

PRIORITY CLAIM

This application is a National Phase Application claiming priority to PCT Application Serial No. PCT/US2017/028027 filed Apr. 18, 2017, which claims priority from U.S. Provisional Application No. 62/341,971, filed May 26, 2016. The disclosure of 62/341,971 is incorporated herein by reference.

FIELD OF THE INVENTION

The present invention relates to processes, systems, and apparatus for making cyclic imide oxidation catalyst, and in particular, N-hydroxyphthalimide (NHPI). The catalyst finds use in many oxidation processes. Of particular interest is the oxidation of cyclohexylbenzene to form cyclohexylbenzene hydroperoxide. Such an oxidation reaction may be employed as part of a process for making cyclohexanone and/or phenol from benzene via hydroalkylation to cyclohexylbenzene.

BACKGROUND OF THE INVENTION

Cyclic imide compounds, and in particular N-Hydroxyphthalimide (NHPI) have many potential uses. In particular, they have shown promise as radical mediators in a number of radical based oxidation reactions, such that these compounds can be used to catalyze oxidation reactions, and in particular to catalyze the oxidation of cyclohexylbenzene to cyclohexyl-1-phenyl-1-hydroperoxide (referred to herein as cyclohexylbenzene-hydroperoxide). As described previously (e.g., in US 2014/0148569, US 2013/0211036, and US 2013/0203984), NHPI-catalyzed oxidation of cyclohexylbenzene is particularly advantaged in a process for making cyclohexanone from benzene via: (i) hydroalkylation of the benzene to cyclohexylbenzene; (ii) oxidation of the cyclohexylbenzene to cyclohexylbenzene-hydroperoxide; and (iii) cleavage of the cyclohexylbenzene-hydroperoxide to phenol and cyclohexanone.

However, although some basic laboratory-scale chemistry is known for the synthesis of NHPI, little is known to date about the commercial scale production of NHPI. See, for instance, U.S. Pat. No. 8,658,804, as well as U.S. Pat. Nos. 4,954,639 and 7,368,615; see also U.S. Patent Publication Nos. 2006/0229196 and 2006/0281629. Thus, it is difficult to obtain quantities of NHPI suitable to catalyze industrial-scale oxidation reactions, such as the aforementioned oxidation of cyclohexylbenzene as part of an industrial-scale process for making cyclohexanone and/or phenol.

There is accordingly a need for processes and systems suitable for making NHPI (and other cyclic imides suitable as oxidation catalysts) on an industrial scale.

Some further references of potential interest in this regard may include: U.S. Pat. Nos. 4,956,168, 5,472,679, 6,299,734, 6,316,639, 7,396,519, and 7,582,774; EP Patent Publication 108294 A, German Patent Publications DE-A-1247282, DE-A-3528463, and DE-A-3601803; Japanese Patent Publications JP 2001-233854, JP 2002-047270, JP 2002-128760, JP 2003-081941, and JP 2004-051626; Chinese Patent Publications CN1051170, CN101845012; and WIPO Publication Nos. WO 95/25090, WO 97/22551, WO 2014/137623, and WO 2016/053583; and the following publications: (1) L. Bauer and O. Exner, "The Chemistry of Hydroxamic Acids and N-Hydroxyimides," Angewandte Chemie, International Edition, Vol. 16, No. 6, pp. 376-384, 1974; (2) W. R. Roderick and W. G. Brown, "Colorless and Yellow Forms of N-Hydroxyphthalimide," Journal of the Amercian Chemical Society, Vol. 79, pp. 5196-5198, 1957; (3) H. Reichelt, C. A. Faunce and H. H. Paradies, "Elusive Forms and Structures of N-Hydroxyphthalimide: The Colorless and Yellow Crystal Forms of N-Hydroxyphthalimide," J. Phys. Chem. A, Vol. 111, pp. 2587-2601, 2007; (4) M. S. Mannan, "Thermal decomposition pathways of hydroxylamine: Theoretical Investigation on the Initial Steps," J. Phys. Chem. A, Vol. 114, pp. 9262-9269, 2010; (5) Y. Iwata, "Study on decomposition of hydroxylamine/water solution," Journal of Loss Prevention in Process Industries, Vol. 16, pp. 41-53, 2003; (6) Y. Iwata, "Decomposition of hydroxylamine/water solution with added iron," Journal of Hazardous Materials, Vol. 104, pp. 39-49, 2003; (7) M. S. Mannan, "Reaction pathways of hydroxylamine decomposition in the presence of acid/base," ISBN: 0-8169-0965-2, Paper 538b, presented Nov. 7-12, 2004 at AIChE Annual Meeting in Austin, Tex.; (8) A. Sakakura, R. Yamashita, T. Ohkubo, M. Akakura and K. Ishihara, "Intramolecular Dehydrative Condensation of Dicarboxylic Acids with Bronsted Base-Assisted Boronic Acid Catalysts," Australian Journal of Chemistry, Vol. 64, No. 11, pp. 1458-1465, 2011; (9) Agrawal, "Dissociation Constants of Some Hydroxamic Acids," Zeitschrift fuer Naturforschung, 1976, Vol. 31B, No. 5, pp. 605-606; (10) Benjamin et al., "The Synthesis of Unsubstituted Cyclic Imides Using Hydroylamine Under Microwave Irradiation," Molecules, 2008, Vol. 13, pp. 157-169; (11) Edafiogho et al., "Synthesis and Anticonvulsant Activity of Imidooxy Derivatives," Journal of Med. Chemistry, 1991, Vol. 34, pp. 387-392; (12) Einhorn et al., "Mild and Convenient One Pot Synthesis of N-Hydroxyimides from N-Unsubstituted Imides," Synthetic Communications, 2001, Vol. 31, No. 5, pp. 741-748; (13) Gross et al., "Zur Darstellung Von N-Hydroxyphthalimid Und N-Hydroxysuccinimid," Journal fur praktische Chemie, 1969, Vol. 311, pp. 692-693; (14) Imai et al., "The Reaction of N-(Mesyloxy)Phthalimide and N-(Mesyloxy)Succinimide With Various Amines," Nippon Kagaku Kaishi, 1975, Vol. 12, pp. 2154-2160; (15) Karakurt et al., "Synthesis of Some 1-(2-Naphthyl)-2-(Imidazole-1-yl) Ethanone Oxime and Oxime Ether Derivatives and Their Anticonvulsant and Antimicrobial Activities," European Journal of Medical Chemistry, 2001, Vol. 36, pp. 421-433; (16) Khan, "Effect of Hydroxylamine Buffers on Apparent Equilibrium Constant for Reversible Conversion of N-Hydroxyphthalimide to o-(N-Hydroxycarbamoyl)-Benzohydroxamic Acid: Evidence for Occurrence of General Acid-Base Catalysis," Indian Journal of Chemistry, 1991, Vol. 30A, pp. 777-783; and (17) Sugamoto et al., "Microwave-Assisted Synthesis of N-Hydroxyphthalimide Derivatives," Synthetic Communications, 2005, Vol. 35, pp. 67-70.

SUMMARY

In some aspects, the present invention relates to forming solid cyclic imide, for instance N-hydroxyphthalimide (NHPI). Processes according to some embodiments include contacting hydroxylamine solution with a cyclic carboxylic acid anhydride so as to form a reaction medium having initial temperature $T_i$ of less than 65° C.; raising the reaction medium temperature to a transition temperature $T_t$ within the range from 65° C. to less than 75° C., thereby forming a first slurry comprising solid intermediate hydroxamic acid within the reaction medium; and further heating the reaction medium to a final temperature $T_f$ within the range from 75°

C. to 200° C., thereby converting at least a portion of the solid intermediate hydroxamic acid to solid cyclic imide.

In certain embodiments, the hydroxylamine solution may be obtained by contacting a hydroxylammonium salt with aqueous base, such as NaOH or $NH_3$. In further aspects, the cyclic carboxylic acid anhydride comprises phthalic anhydride, the solid intermediate hydroxamic acid comprises N-hydroxyphthalamic acid (NHPA), and the cyclic imide comprises NHPI.

Processes in accordance with yet further aspects include a continuous and/or semi-batch reaction. Such reaction may comprise continuously feeding hydroxylamine solution and carboxylic acid anhydride (e.g., phthalic anhydride) to a continuous flow reactor via one or more feed inlets, so as to establish a reaction medium flowing continuously in a downstream direction within the reactor; at a second location along the reactor that is downstream of the one or more feed inlets, feeding steam or water into the reaction medium; at a third location along the reactor that is downstream of the second location, feeding additional steam or additional water into the reaction medium; agitating the reaction medium within the reactor between the second and third locations; and recovering a reaction product comprising solid cyclic imide (e.g., NHPI) from the reaction medium.

The solid cyclic imide (e.g., NHPI) in processes according to some embodiments is recovered from a reaction product comprising solid cyclic imide in mother liquor. The reaction product may be provided to a solid/liquid separation system so as to obtain the solid cyclic imide and a waste water effluent. The waste water effluent may be further treated and/or recycled to the reaction. The solid cyclic imide may be utilized in an oxidation reaction, and in particular embodiments it may be contacted with cyclohexylbenzene and an oxygen-containing gas so as to obtain cyclohexyl-1-phenyl-1-hydroperoxide.

DETAILED DESCRIPTION

Figure 1:
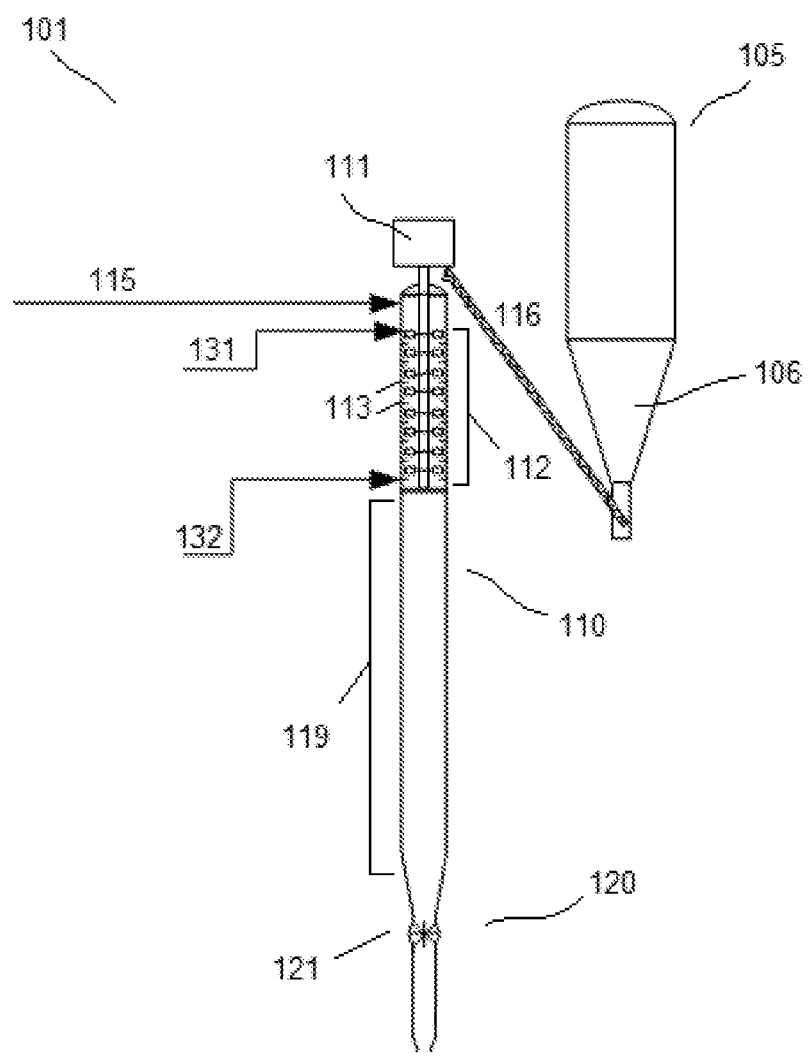
FIG. 1 is a schematic diagram of a process and system for reacting hydroxylamine and cyclic carboxylic acid anhydride in accordance with some embodiments.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

Various embodiments described herein provide a process for making a cyclic imide, such as N-hydroxyphthalimide (NHPI). Taking the example of NHPI, such processes may include: (1) obtaining reactable hydroxyl amine; (2) contacting the reactable hydroxylamine with phthalic anhydride so as to form N-hydroxyphthalamic acid (NHPA); and (3) heating the NHPA so as to obtain NHPI. Each of the aforementioned elements of such processes is discussed in further detail below.

Obtaining Reactable Hydroxylamine

"Reactable hydroxylamine" refers to hydroxylamine in suitable form for reaction with phthalic anhydride so as to form NHPA. Hydroxylamine ($NH_2OH$) is susceptible to being protonated into the corresponding hydroxylammonium ion ($NH_3OH^+$), which in turn forms ionic bonds with a salt. However, it is the hydroxylamine itself, not a hydroxylammonium salt, that should be reacted with the phthalic anhydride.

In processes according to some embodiments, reactable hydroxylamine may be obtained in the form of a salt-free water solution, which may also be referred to as hydroxylamine free base (HAFB), which may be purchased or otherwise acquired (for instance, a 50% HAFB aqueous solution is commercially available from BASF SE). Such hydroxylamine solution may comprise (a) 1 wt % to 70 wt % hydroxylamine (such as 5 to 15 wt %, 15 to 30 wt %, or 30 to 70 wt %, with ranges from any lower limit to any upper limit also contemplated), (b) water, and (c) less than 1 wt % of compounds other than hydroxylamine and water.

Processes of yet other embodiments include forming an aqueous solution of hydroxylamine base. For instance, sodium hydroxide (NaOH) and/or other strong bases (e.g., potassium hydroxide (KOH), lithium hydroxide (LiOH), calcium hydroxide ($Ca(OH)_2$), barium hydroxide $Ba(OH)_2$, magnesium hydroxide ($Mg(OH)_2$), and/or strontium hydroxide ($Sr(OH)_2$) may be added to an aqueous solution of hydroxylammonium salt (e.g., aqueous hydroxylammonium sulfate), as shown in the reaction pathway (1) below. It will be appreciated that another hydroxylammonium salt may be used instead of, or in addition to, hydroxylammonium sulfate (e.g., the chloride, nitrate, and/or phosphate hydroxylammonium salts, among others). Generally, suitable hydroxylammonium salts having melting points (measured at 1 atm pressure) of 100° C. or higher, such that they are solid at 25° C., 1 atm pressure.

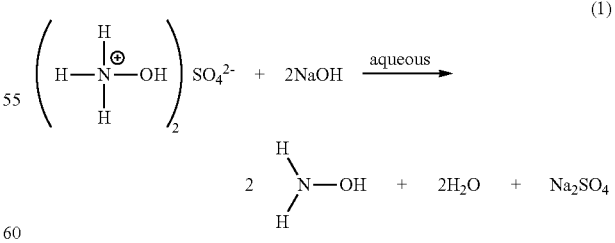

(1)

Alternatively, ammonia ($NH_3$) or another weak base (e.g., methylamine, ethylamine, dimethylamine, diethylamine, methylethylamine (MEA), trimethylamine, triethylamine, sodium acetate, other carboxylic acid salts, sodium carbonate, sodium bicarbonate, sodium hypochlorite, sodium phosphate, sodium hydrogen phosphate, and the same salts with potassium instead of sodium) may be added to the aqueous hydroxylammonium salt solution, as shown in the reaction pathway (2) below.

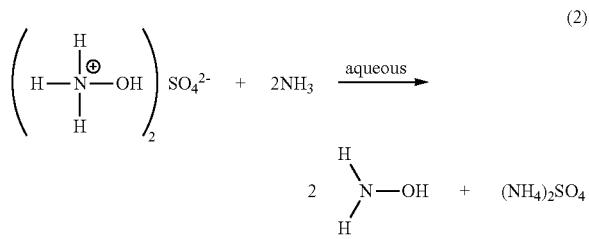

As indicated in each of reaction pathway (1) and (2), both reactions result in an aqueous hydroxylamine solution (also comprising an ionic-bonded salt).

In yet further embodiments, hydroxylamine solution may be formed by contacting an aqueous solution comprising hydroxylammonium salt (e.g., hydroxylammonium sulfate) with a strongly basic ion exchange resin. Examples of suitable strongly basic ion exchange resins are those which comprise a hydroxyl group, such that it makes OH⁻ available as a base (similar to the strong base NaOH). More particular examples include strong base, type 1, anionic resins, for instance macroreticular polymeric resins. For example, Amberlyst™ A26 resin, available from the Dow Chemical Company, is such a resin in which the polymeric resin is based on crosslinked styrene divinylbenzene copolymer containing positively charged quaternary ammonium groups. Ionically bonded hydroxyl ions are part of the resin structure for charge neutrality. In some embodiments, an anionic exchange resin may also have a porous structure, which may be beneficial for use in both aqueous and non-aqueous media. Further, an anionic exchange resin having a macroreticular structure and pore size distribution may impart beneficial resistance to mechanical and osmotic shock.

In yet other embodiments, the hydroxylamine solution may be formed by contacting an aqueous solution comprising hydroxylammonium salt with a weakly basic ion exchange resin (e.g., Amberlyst™ A21 resin, available from the Dow Chemical Company, or Lewatit™ MP62WS, available from Lanxess AG). Such resins would function similarly to ammonia solution in forming hydroxylamine solution according to some embodiments. The weakly basic ion exchange resins of some embodiments may more generally comprise polymeric material comprising one or more neutral ternary amine groups, such that the amine groups function as weak bases similarly to free ammonia.

In embodiments in which hydroxylamine solution is formed, the temperature in solution during formation of the hydroxylamine should remain at 40° C. or below, preferably 37° C. or below, more preferably 35° C. or below, which is understood to help avoid excessively fast decay of the hydroxylamine product during reaction. Because the reaction of hydroxylammonium salt and aqueous base is exothermic, some embodiments include processes for managing the temperature of the reaction for forming hydroxylamine solution. For instance, the aqueous base may be maintained at temperatures of 25° C. or lower, preferably 20° C. or lower, more preferably 15° C. or lower prior to contacting the hydroxylammonium salt. Also or instead, a heat exchanger may be used (e.g., around a reaction vessel in which the hydroxylamine solution is formed). However, due to the corrosive nature of the reaction material, it is preferable to control the heat of the aqueous base so as to maintain reaction temperature within the aforementioned ranges.

Also or instead, in certain embodiments, the pH of the solution during formation of the hydroxylamine preferably remains within the range from 8 to 10; however, lower ranges may be acceptable in some embodiments (e.g., ranging from 3 to 10, such as from 5 to 10). Further, it is preferred that the hydroxylammonium salt and added base be reacted with each other in amounts such that the hydroxylamine-equivalent mole ratio of (i) hydroxylammonium salt to (ii) added base (either strong, e.g., NaOH, or weak, e.g., $NH_3$) in the solution be within the range from 0.5 to 1.5, such as 0.8 to 1.2, for formation of the hydroxylamine. The term "hydroxylamine-equivalent mole ratio" means that the number of moles of hydroxylammonium salt is multiplied by the number of moles of hydroxylamine released from the hydroxylammonium salt during reaction with the added base (e.g., NaOH, $NH_3$, or other base). Thus, in the case of hydroxylammonium sulfate, $(NH_3OH)_2SO_4$, two moles of hydroxylamine are released per one mole of hydroxylammonium sulfate. Thus, 1 mole of hydroxylammonium sulfate equals 2 "hydroxylamine-equivalent" moles for purposes of computing the hydroxylamine-equivalent mole ratio of the hydroxylammonium sulfate salt to the base.

In some embodiments, use of a weak base, and in particular ammonia, is preferred in forming the aqueous hydroxylamine solution. For instance, use of ammonia or another weak base may help keep the solution within preferred pH ranges during formation of the hydroxylamine, and/or maintain temperature sufficiently low (e.g., within the preferred ranges noted above), particularly since ammonia has a smaller exotherm in reacting with hydroxylammonium salts like hydroxylammonium sulfate, as compared to reaction between NaOH (or another strong base) and hydroxylammonium salts. This means that a weak base can be added to the hydroxylammonium salt solution at a higher rate than a corresponding strong base (e.g., NaOH), due to the lesser degree of heat generation, while still maintaining temperature adequately low to prevent decomposition of the desired hydroxylamine product.

Reaction of Hydroxylamine and Phthalic Anhydride

As noted, once the hydroxylamine solution (preferably aqueous hydroxylamine solution) is obtained as the reactable hydroxylamine, the process of some embodiments further includes contacting the hydroxylamine with phthalic anhydride so as to form a liquid reaction medium (preferably an aqueous liquid reaction medium). Advantageously, the ensuing reaction steps do not require separation of byproduct salts from the hydroxylamine solution. "Byproduct salts" refer to salts formed during reaction of hydroxylammonium salt and base, such as a sulfate salt when hydroxylammonium sulfate is the starting hydroxylammonium salt, and more particularly ammonium sulfate when ammonia is the base reacted with hydroxylammonium sulfate to form hydroxylamine That is, the aqueous hydroxylamine solution according to some embodiments comprises byproduct salts when it is contacted with phthalic anhydride to form the liquid reaction medium. Preferably, such byproduct salts are as soluble in water as possible, which makes for greater ease of eventual separation of the byproduct salts from solid NHPI product (discussed in greater detail below). According to yet other embodiments, however, the hydroxylamine solution contains fewer than 1 wt %, preferably 0.5 wt % or less, such as 0.1 wt % or less, of byproduct salts (e.g., as is the case following separation of the salts; or as is the case when hydroxylamine free base is obtained for use in the following reaction with phthalic anhydride).

Preferably, both hydroxylamine solution and phthalic anhydride are provided to a reaction zone (e.g., in pre-mixed feed or via separate feed mechanisms) in continuous, batch, or semi-batch fashion. In some embodiments, the hydroxylamine solution and phthalic anhydride are provided in amounts such that the mole ratio of hydroxylamine to phthalic anhydride is within the range from 0.5 to 2, more preferably 0.9 to 1.7, such as 1.1 to 1.5.

However the hydroxylamine is contacted with the phthalic anhydride, the reaction medium is preferably agitated so as to help maximize the conversion of phthalic anhydride. Further, the reaction according to various embodiments proceeds in two phases (with agitation continuing during both phases in some embodiments).

In the first reaction phase according to some embodiments, hydroxylamine solution and phthalic anhydride are contacted so as to react as completely as practicable (e.g., preferably achieving 90 wt %, more preferably 95 wt %, most preferably 99 wt % or more, such as 100 wt % conversion of phthalic anhydride). The product of this reaction is solid N-hydroxyphthalamic acid (NHPA), which forms a paste-like slurry in the aqueous solution reaction medium. However, phthalic anhydride can also be hydrolyzed to phthalic acid during the course of this reaction. Accordingly, two competing temperature preferences are at play during this first phase reaction: on the one hand, it is preferred to maintain temperature of the reaction medium during this first phase reaction below 75° C., preferably less than or equal to 70° C., more preferably less than or equal to 67° C., so as to minimize the conversion of phthalic anhydride to the undesired byproduct phthalic acid; on the other hand, it is also desirable to gradually raise the temperature of the reaction medium to a transition temperature $T_t$ within the range from a low of 65° C. to a high of less than 75° C. This is because achieving such a transition temperature $T_t$ in the reaction medium allows one to approximate that most of the phthalic anhydride has been reacted (e.g., it is likely that phthalic anhydride conversion is 90 wt % or more, preferably 95 wt % or more, most preferably 99 wt % or more, such as 100 wt %).

Therefore, the first-phase reaction according to such embodiments comprises: (a) contacting hydroxylamine solution (preferably aqueous hydroxylamine solution) and phthalic anhydride so as to establish a reaction medium (preferably a liquid solution reaction medium) having an initial temperature $T_i$ of less than 65° C., such as within the range from 15° C. to 65° C., preferably from 20° C. to 55° C., more preferably from 25° C. to 40° C. (with ranges from any lower end-point to any upper end-point also contemplated in various embodiments); and (b) raising the reaction medium temperature (preferably while agitating the reaction medium) to a transition temperature $T_t$ within the range from 65° C. to less than 75° C. (i.e., 65° C. $<T_t<$ 75° C.). In some embodiments, the raising (b) is carried out at a rate within the range from 0.01 to 500° C./min, such as 0.1 to 100° C./min Preferably, the heating rate at this stage is within the range from 0.4° C. to 50° C., such as 0.5° C. to 20° C.; however, heating rates within ranges from any aforementioned lower limit to any upper limit are also contemplated in various embodiments.

The phthalic anhydride in the contacting (a) is preferably in solid form. According to other embodiments, however, phthalic anhydride is maintained in its molten state for ease of storage and conveying to the reaction; however, given the high melting point of phthalic anhydride (131° C.), such embodiments preferably also include cooling means—e.g., use of a heat exchanger and/or addition of cold (10° C. or less) water to form a slurry of phthalic anhydride. A heat exchanger is preferable given the possible reaction of phthalic anhydride to phthalic acid to water.

Because the reaction between phthalic anhydride and hydroxylamine is exothermic, some of the heat needed to raise the reaction medium temperature to the transition temperature $T_t$ may be provided by the reaction itself; however, in some embodiments, additional heat is provided to the reaction medium. This additional heat may be provided in any suitable manner. In some embodiments, the heat is provided to the reaction medium during the first phase reaction in the form of heat exchangers (e.g., through use of a heating jacket around a reactor), and/or it may be provided through addition of hot water and/or steam to the reaction medium. As will be discussed in more detail below, some preferred embodiments include the use of steam to provide heat to the reaction medium during this first phase.

In various embodiments, the reaction medium at this point is a paste-like first slurry comprising solid NHPA. Preferably, the paste-like slurry is an aqueous slurry, and in addition to the NHPA and water, it may also comprise byproduct salts (the presence of which was previously noted within the hydroxylamine solution of some embodiments) and byproduct phthalic acid (formed during the reaction of phthalic anhydride).

In the second phase of the reaction according to some embodiments, the first slurry comprising the intermediate NHPA is further brought to a final temperature $T_f$ within the range from 75° C. to 150° C., preferably 80° C. to 120° C., most preferably 85° C. to 95° C. (with any lower limit to any upper limit contemplated in various embodiments). This heating brings about conversion of the NHPA to the desired solid NHPI product. Heating to a $T_f$ above 150° C. is also contemplated in some embodiments (e.g., to 200° C. or even up to 300° C.), although it is considered not necessary to achieve the desired conversion of NHPA to NHPI. Further, according to some embodiments, it is preferred that the $T_f$ range be below 230° C., preferably below 220° C., to as to maintain the NHPI product in solid form, given the 233° C. melting point of NHPI.

As NHPA is converted to NHPI, the first slurry of the reaction medium transitions to a second slurry that is more difficult to agitate; thus, some embodiments include the addition of water, steam, or other fluid (inert to the hydroxylamine-phthalic anhydride reaction) to the reaction medium slurry (such fluid may be added before, during, or after the heating of the second phase, preferably before or during). In some preferred embodiments, the addition of water and/or steam is used both to further heat the reaction medium and to render the first and/or second slurries more easily agitated. In yet other embodiments, however, water may be added to increase stirability without necessarily increasing temperature. In fact, water added to increase stirability may in some embodiments lead to a reduction of the reaction medium temperature (e.g., where added water is of lower temperature than the reaction medium); in such instances, heat is separately provided (e.g., by heat exchange means such as a heating jacket or the like, as is known in the art) to then raise the temperature to the desired $T_f$.

Accordingly, the process of some embodiments further comprises, after the previously-noted (b) raising the reaction medium temperature to $T_t$, (c) further heating the reaction medium to the final temperature $T_f$ (according to the above-recited ranges for $T_f$), thereby converting at least a portion, preferably at least 80 wt %, more preferably at least 90 wt %, even more preferably at least 95 wt %, of the NHPA to NHPI. In certain of these embodiments, the (c) further heating comprises adding water and/or steam to the reaction medium. pH is preferably maintained at or above 3.5, such as 4.0 or higher, during this heating. Likewise, pH of the second slurry comprising NHPI is preferably maintained at or above 3.5, such as at 4.0 or higher.

The heating rate may be rapid (e.g., the process may comprise heating the reaction medium at a rate within the range of 0.01° C./min to 1000° C./min, preferably 300° C./min to 750° C./min, more preferably 400° C./min to 750° C., with ranges from any lower limit to any upper limit also contemplated in various embodiments). Further, the reaction medium according to some embodiments may be maintained at a temperature within any of the foregoing ranges noted as suitable for final temperature $T_f$ for a period of time (e.g., at least 5, preferably at least 12, more preferably at least 15 minutes, or in some embodiments within the range from 0 to 60 min) to ensure maximum conversion of NHPA to NHPI. In some embodiments, this can be accomplished through lapse of time between heating and removal of product (e.g., in a batch reactor) or, in other embodiments, through controlling flow rate in a continuous flow reactor (e.g., a down-flow reactor) so as to achieve a residence time within one of the foregoing time ranges in a portion of the continuous reactor in which the temperature of the reaction medium is within the foregoing ranges for $T_f$.

Batch, Semi-Batch, and Continuous Reaction

NHPI-forming reactions in accordance with various embodiments may be carried out in batch, semi-batch, or continuous reaction modes.

For instance, in a batch or semi-batch reaction according to some embodiments, the hydroxylamine solution and phthalic anhydride are provided to one or more batch reaction zones so as to form a reaction medium in each reaction zone. Each batch reaction zone may comprise a stirred tank reactor or any other suitable reactor device capable of agitating the reaction medium. Each reactor device may comprise a heating jacket, heating coils, or the like disposed on an outer surface of the reactor, and/or a water or steam feed conduit capable of delivering water and/or steam to the reaction medium in each batch reactor, so as to enable temperature control of the reaction medium. Alternatively (or in addition), the inlet feed conduit may be provided with a heat exchanger or the like to control inlet feed temperatures (and thereby help control reaction medium temperature). Each reaction zone temperature is preferably monitored so as to ensure initial temperature $T_i$ of the reaction medium is initially maintained within the ranges specified previously. Temperature monitoring may be by any suitable means in the art (e.g., direct measuring and/or calculation based on inlet and outlet temperatures, or the like). To the extent different means of monitoring temperature within a liquid reaction medium may differ in their results, the following means of measuring temperature in the reaction medium in the batch reactor should govern for purposes of determining temperature in a batch or semi-batch reaction medium according to various embodiments described herein: given the continuous agitation of the reaction medium, temperature may be measured directly using one or more temperature probes (preferably Teflon-coated type J or type K thermocouple, with no need for a thermowell) inserted anywhere in the reaction medium, so long as each probe is inserted into the reaction medium such that it has no physical contact with a reactor wall, mixing apparatus, or other component of the reactor (i.e., such that the probe is immersed in, and surrounded by, the reaction medium). Where multiple temperature probes are used to determine temperature of the batch or semi-batch reaction medium, the average (mean) temperature of each probe may be taken as the reaction temperature.

In yet other embodiments, the reaction may be carried out in semi-batch or continuous mode in a reaction system such as the system 101 illustrated in FIG. 1, operation of which will be described in connection with that figure. Hydroxylamine solution (preferably at 40° C. or less, more preferably 37° C. or less, as described previously) may be supplied to a down-flow reactor 110 in a continuous or semi-batch (e.g., sporadic and metered) manner via hydroxylamine feed conduit 115. Solid phthalic anhydride can be stored in any suitable storage unit (e.g., silo 105 comprising hopper 106 in a bottom portion thereof), metered from the storage unit 105, and fed to the reactor 110 via feed conveyor 116. Feed conveyor 116 may be any suitable means for conveying solid feed to the reactor 110, such as a screw conveyor, drag chain, vibratory conveyor, belt conveyor, bucket conveyor, pneumatic conveyor, or other like conveyor. Preferably, feed conveyor 116 enables continuous flow of solid phthalic anhydride feed to the reactor 110, and it furthermore prevents passage of liquid from the reactor 110 to the storage unit 105. Feed conveyor 116 as illustrated in FIG. 1 is a screw-type conveyor.

Many forms of reactors capable of mixing or otherwise agitating the reactor contents could be used in processes according to various embodiments. Illustrated in FIG. 1 is a down-flow reactor 110 equipped with a plurality of rotary mixing blades 112 that are turned by a motor 111. The rotary mixing blades 112 are interposed between donut-shaped baffles 113 extending inward from the reactor wall into the inner reactor space, creating a set-up akin to a disk-and-donut reactor design (in which the disks are replaced by rotary mixing blades 112). In alternatives according to some embodiments, a disk-and-donut design may instead be used (in which disks, stationary or rotating, are employed in place of the rotary mixing blades 112). Horizontal reactor designs could alternatively be used, as well. Preferably, the reactor is capable of permitting flow of the reactor contents in a downstream direction (e.g., from phthalic anhydride and hydroxylamine feed inlet(s) to product outlet 120), while also being capable of agitating the reactor contents in a direction that is at least partially perpendicular to the downstream flow of reactor contents (e.g., such that at least some portion of mass transfer as a result of the agitation occurs in a direction that is represented by a vector having an angle between 80° and 100° relative to the downstream direction). As illustrated in FIG. 1, the downstream direction in the down-flow reactor 110 is downward (i.e., in the direction of gravity), and the rotary mixing blades 112 and baffles 113 provide horizontal/radial agitation of the reaction medium within the upper portion of the reactor 110. As also illustrated in FIG. 1, the reactor 110 of some embodiments may include a downstream portion 119 in which the mixing apparatus is not disposed.

As the hydroxylamine solution and phthalic anhydride are fed into the top of the down-flow reactor 110, the reaction medium in the upper portion of the reactor in some embodiments has initial temperature $T_i$ in accordance with the previously-described ranges of $T_i$. The reaction medium according to some embodiments will, at this point in the reactor, comprise liquid solution. The mixing apparatus may or may not be disposed in this upper portion of the reactor 110; as illustrated in FIG. 1, the mixing apparatus is not disposed in this upper portion of the reactor 110. At a point downstream of the feed (hydroxylamine solution and phthalic anhydride feed) inlet(s) to the reactor 110, heating is provided to the reaction medium within the reactor 110. In embodiments in accordance with FIG. 1, providing heating to the reaction medium comprises feeding steam to the reactor 110 (e.g., via first steam conduit 131), although it will be appreciated that hot water (preferably having temperature greater than the initial temperature $T_i$ of the reaction medium) may be utilized instead or in addition. Temperature of steam provided at this point preferably is within the range from 100° C. to 500° C., such as from 100° C. to 250° C., or 100° C. to 150° C., with ranges from any lower limit to any upper limit contemplated in various embodiments. Temperature of hot water provided at this point preferably is within the range from about 50° C. to 100° C. As illustrated in FIG. 1, mixing of the reaction medium begins at this point in the downstream flow of the contents within the reactor 110. As the reaction medium heats and conversion of the phthalic anhydride to NHPA increases, the reaction medium will become a first slurry or paste (e.g., within the portion of the reactor 110 in which the rotary mixing blades 112 are disposed, i.e., the portion downstream of the inlet of the first steam conduit 131 and upstream of the inlet of the second steam conduit 132). Advantageously, use of steam or water to provide the heat to the reaction medium also serves to make this paste-like reaction medium more easily agitated. According to some embodiments, in this portion of the reaction medium flowing through the portion of the reactor 110 in which the rotary mixing blades 113 are disposed, temperature of the reaction medium is increased according to the rates of heating from initial temperature $T_i$ to transition temperature $T_t$ previously described.

At a point downstream of the inlet of the first steam conduit 131, a second steam conduit 132 provides additional steam to the reaction medium within the reactor 110. The additional steam may have temperature according to any of the ranges previously noted with respect to steam provided by the first steam conduit 131. Alternatively, hot water may be provided in this second conduit 132, having temperature within the range from 70° C. to 100° C. In some embodiments, the portion of the reaction medium to which the additional steam is fed is at a transition temperature $T_t$ (within any of the above-described ranges of $T_t$). As such, it can be approximated that high conversion of the phthalic anhydride (e.g., at least 90, 95, 99, or 100 wt %) of the phthalic anhydride has been achieved in this portion of the reaction medium. Preferably, the distance between the inlets of the first and second steam conduits 131 and 132, respectively, is such that residence time of the reactor contents between said first and second steam feeds allows for the highest practicable conversion of phthalic anhydride to NHPA, while also permitting sufficiently slow heating to minimize side reactions of the phthalic anhydride to phthalic acid. The ordinarily skilled artisan will recognize that various parameters may be adjusted instead of or in addition to distance between the inlets of steam conduits 131 and 132, e.g., flow rate of reactor contents and flow rates of the respective steam feeds. In certain embodiments, the distance between steam feeds, flow rates, and/or other design factors are such that the previously described heating rate of the reaction medium from initial temperature $T_i$ to transition temperature $T_t$ is maintained within the portion of the reaction medium flowing from the inlet of the first steam conduit 131 to the inlet of the second steam conduit 132, and further such that the reaction medium has reached transition temperature $T_t$ at the point at which the second steam conduit 132 provides the additional steam to the reaction medium. Further, although not illustrated in FIG. 1, in certain embodiments, additional conduits may deliver additional steam and/or water feeds to the reaction medium so as to establish a desired temperature profile within the flowing reaction medium.

The additional steam according to some embodiments heats the reaction medium to the final temperature $T_f$, thereby converting the NHPA in the reaction medium to NHPI.

The reaction medium then flows downstream through the reactor 110 in a downstream portion 119 in which the flow regime approaches plug flow. Just downstream of the inlet of the final steam conduit 132, convection currents continue to distribute heat through the reaction medium, converting NHPA to NHPI. As this conversion takes place, the reaction medium transitions from the first paste or slurry to a second paste or slurry comprising NHPI as it flows through the reactor 110. Farther downstream within the downstream portion 119, the reaction medium begins to cool once again; this further cooling may help additional solid NHPI precipitate out of the second slurry. The second slurry then exits the reactor through outlet 120, preferably via a rotary valve 121 or other means suitable for conveying the second slurry or paste in continuous flow through the outlet 120, after which the solid NHPI product is separated from the mother liquor in the second slurry (described in more detail below).

Accordingly, processes in accordance with embodiments carried out in the system illustrated in FIG. 1 may be summarized more generally as comprising: (a) feeding hydroxylamine solution and phthalic anhydride to a reactor via one or more feed inlets, so as to establish a reaction medium flowing in a downstream direction within the reactor; (b) at a second location along the reactor that is downstream of the one or more feed inlets, feeding steam into the reaction medium; (c) at a third location along the reactor that is downstream of the second location, feeding additional steam into the reaction medium; (d) agitating the reaction medium within the reactor between the second and third locations; and thereafter (e) recovering a reaction product comprising NHPI from the reaction medium. Optionally, the reaction medium can be agitated upstream of the second location and/or downstream of the third location, as well. In some embodiments, the reaction medium upstream of the second location (i.e., upstream of the first feeding point of the steam) will comprise liquid solution (comprising hydroxylamine and phthalic anhydride); the reaction medium will comprise a slurry or paste (comprising NHPA) in a portion of the reaction medium downstream of the second location and upstream of the third location; and the reaction medium will comprise a second slurry or second paste downstream of the third location. In certain of these embodiments, the reaction medium approaches plug flow in the portion of the reaction medium downstream of the third location (i.e., downstream of the second steam feed location).

Controlling the Reaction

It should be noted that processes according to many of the above-described embodiments are not limited to or even necessarily associated with reaction medium temperatures (e.g., the initial temperature $T_i$, transition temperature $T_t$, and final temperature $T_f$ described previously). For instance, in the case of semi-batch or continuous reactions according to some embodiments, maintaining flow of the reaction medium in a downstream direction while feeding steam and/or hot water to the reaction medium at the second and third locations allows for flexible design of the process conditions (e.g., flow rate within the reactor, inlet steam flow rate(s), and/or distance between the second and third locations at which first and second steam feeds, respectively, are provided) so as to achieve adequate heating and mixing of the reaction medium between the two steam feed locations. Such adequate heating and mixing preferably achieves the goals of (i) highest practicable conversion of phthalic anhydride to NHPA in the reaction medium while (ii) minimizing the side reaction of phthalic anhydride to phthalic acid. The ordinarily skilled artisan, equipped with the knowledge provided herein, will readily be able to design reaction medium flow rate (e.g., residence time), reactor agitation, distance between steam feeds, and steam flow rates so as to ensure maximum conversion of phthalic anhydride to NHPA while minimizing phthalic acid formation upstream of the second steam feed point (i.e., the third location in the above summary of processes according to some embodiments). For instance, a target heating rate may be set (e.g., within the target heating rates according to some embodiments described previously with reference to the heating from initial temperature $T_i$ to transition temperature $T_t$), and one or more of first steam feed flow rate, reaction medium flow rate, and reaction agitation, may be designed so as to approximate that target heating rate. And, rather than necessarily requiring attention to reaction medium temperature, the product can simply be analyzed to determine if excessive phthalic acid is present (in which case reaction medium flow rate can be slowed, and/or distance between steam feed points increased, and/or agitation modified to increase mass transfer within the reaction medium between the steam feed points). Or, if unreacted phthalic anhydride remains in the product, steam flow rate in the first steam feed (i.e., at the second location in the above summary) can be increased, and/or reaction medium flow rate decreased, so as to ensure more complete heating.

Nonetheless, in yet other embodiments, providing heat to the reaction medium may be associated with reaction medium temperature, and could even be controlled in a real-time manner (e.g., using actuator-controlled valves or like means to decrease or increase feed rates of steam, hydroxylamine solution, and/or phthalic anhydride, based at least in part upon measured temperature within the reaction medium). For instance, in processes according to such embodiments, a first temperature probe may be inserted into the reactor at a location that is both (i) upstream of the inlet of the first steam conduit 131 and (ii) at a location along the length of the reactor that is within 0.05 D meters downstream from the inlet of the hydroxylamine solution feed conduit 115 (where D is the total length of the reactor, e.g., height of a down-flow reactor or lateral length of a horizontally disposed reactor). The first temperature probe is inserted such that it is immersed in the flowing reaction medium during normal operation of the reactor 110, and therefore can measure a first temperature of the reaction medium. Preferably, the process in such embodiments is controlled such that the first temperature of the reaction medium is within one or more of the ranges for initial temperature $T_i$, given previously. Likewise, a second probe may be inserted into the reactor 110 at a location that is between 0.01 D meters and 0.05 D meters upstream from the inlet of the second steam feed conduit 132, so as to be immersed in the flowing reaction medium during normal operation of the reactor 110, enabling measurement of a second temperature of the reaction medium. Preferably, the process in such embodiments is controlled such that the second temperature of the reaction medium is within one or more of the ranges for transition temperature $T_t$ given previously. Finally, a third probe may be inserted into the reactor 110 at a location that is between 0.03 D and 0.08 D meters downstream from the inlet of the second steam feed conduit 132, so as to be immersed in the flowing reaction medium during normal operation of the reactor 110, enabling measurement of a third temperature of the reaction medium. Preferably, the process of such embodiments is controlled such that the third temperature is within one or more of the ranges for final temperature $T_f$ given previously. In embodiments in which more than two steam inlets are used to create a desired temperature profile within the reactor, final temperature $T_f$ is instead measured at a point that is between 0.03 D and 0.08 D meters downstream from the inlet of the final steam feed conduit. It should be noted that other means suitable in the art for determining temperature profile within the reaction medium may instead be employed to determine whether the initial, transition, and final temperatures are reached within the various points of the reaction medium; however, to the extent such methods may provide significantly different results (i.e., differences greater than the ordinarily skilled artisan would expect from experimental error), it is preferred to use the temperature measurement methods described herein.

In yet other embodiments of semi-batch or continuous operation similar to the reactor system 101 illustrated in FIG. 1, instead of (or in addition to) providing heat through steam and/or water feeds, the reactor 110 could be equipped with a heating jacket, heating coils, or other like heat exchange means capable of providing heat to the reaction medium. However, heating via steam/water feeds is preferred for at least three reasons:

(1) Due to the corrosive nature of hydroxylamine, the interior walls of all process pipes and vessels in which hydroxylamine is or may be present (e.g., reactor 110) must be polymer-lined (for example, polytetrafluoroethylene (e.g., Teflon coatings), polyethylene, polypropylene, or the like), and such polymer lining drastically reduces the efficiency of heat exchange across such vessel walls;

(2) As noted previously, the steam and/or water provide the extra advantage of rendering the reaction medium within the reactor 110 more easily agitated as the reactor contents become more paste-like during the course of the reaction; and (3) It is believed that water and/or steam addition advantageously helps maintain in solution (i.e., prevents the precipitation of) any byproduct phthalic acid generated during the reaction (e.g., through hydrolysis of phthalic anhydride to phthalic acid), as well as any other salt impurities (such as sulfate, chloride, or other salts corresponding to the hydroxylammonium sulfate, hydroxylammonium chloride, or other hydroxylammonium compound) used in forming the hydroxylamine.

Expanding further on the noted third advantage of water and/or steam addition according to certain embodiments, hydroxylammonium sulfate and ammonia may be preferred reactants for forming the hydroxylamine in various embodiments, as the corresponding ammonium sulfate salt byproduct formed from that reaction has advantageously high solubility in water. Thus, in general, it is preferred that the byproduct of the hydroxylammonium salt and base reaction be as highly soluble in water as possible, so as to make removal by water washing as efficient as possible (e.g., such that less water overall is required to remove the same amount of byproduct). This will help minimize wastewater generated in washing the solid NHPI product, discussed in greater detail below.

In yet further embodiments, the reaction medium may be monitored for transition between reaction phases by means other than temperature, product composition analysis, or the like. For instance, viscosity of the reaction medium may be monitored to determine the point within a continuous flow reactor (or the time during operation of a batch reactor) at which the first slurry comprising NHPA intermediate forms; heat can then be provided to form the second slurry comprising NHPI. Optionally, the reaction medium viscosity may be measured to confirm formation of the second slurry following the addition of heat. Other online physical measurements may also or instead be carried out (e.g., density, online particle analyzing, online IR, Raman, particle counters, reflective measurements, online NMR, X-ray, radar, or the like). Such processes may therefore comprise contacting hydroxylamine solution and phthalic anhydride to form a liquid solution reaction medium; allowing the hydroxylamine and phthalic anhydride to react so as to form a first slurry comprising NHPA (while maintaining temperature in the liquid solution and in the first slurry at less than 75° C., preferably 70° C. or less, more preferably 67° C. or less); and heating the first slurry to convert at least a portion (preferably at least 85 wt %, more preferably at least 90, 95, 99, or even 100 wt %) of the NHPA to NHPI, thereby forming a second slurry comprising the solid NHPI. Heating the first slurry may comprise heating to a final temperature $T_f$ according to any one or more of the previously described ranges for $T_f$.

Multiple Reaction Zones

In yet further embodiments, the above-described processes may take place in multiple reaction zones. Advantageously, such reaction zones may be split according to the stages of the reaction. For instance, some such embodiments include a first reaction zone capable of receiving hydroxylamine solution and phthalic anhydride feed, and be controlled to have inlet temperature within any one or more of the ranges for initial temperature $T_i$ previously described. The first reaction zone is further controlled so as to maintain temperature below 75° C., preferably 70° C. or less, or 67° C. or less. The first slurry comprising NHPA is formed in the first reaction zone, and then conveyed by any suitable means to a second reaction zone. The second reaction zone is operated to heat the first slurry to convert at least a portion of the NHPA (preferably at least 85 wt %, more preferably at least 90, 95, 99, or even 100 wt %) to NHPI, thereby forming the second slurry.

Alternatively, in other embodiments, each reaction zone may be controlled based upon viscosity of the reaction medium, and/or pre-calculated residence times, rather than based upon reaction medium temperatures, similar to embodiments described previously.

Recovering Solid NHPI Crystals

The solid crude NHPI crystals resulting from reactions according to various of the above-described embodiments may be removed from the second slurry by filtration, draining, or the like, and they may further be dried (e.g., oven dried), or processed in any other manner known for the removal of solid reaction products from a mother liquor.

The removal of crude NHPI crystals from the slurry leaves a first wastewater effluent, the handling of which is discussed in more detail below.

In addition, processes of some embodiments further comprise washing the crude NHPI crystals with cold water (0° C. to 10° C., such as 2° C. to 6° C., preferably 3° C. to 5° C.) to remove various organic and inorganic impurities from the crystals. Such a wash should be sufficient to obtain high purity NHPI crystals, particularly if water and/or steam were added to the first slurry comprising the NHPA, thereby helping to maintain various impurities in solution.

Water washing may be particularly advantageous in embodiments wherein the reactable hydroxylamine was obtained by, e.g., reaction between hydroxylammonium salt and base. Such reactions may result in several impurities present in the mother liquor (and thus on crude, unwashed NHPI crystal product), including ions (e.g., sodium and/or ammonium ions, or others, depending on the base used in forming reactable hydroxylamine), salts (e.g., sulfate where hydroxylammonium sulfate is the hydroxylammonium salt), water, phthalic acid, and other organic impurities. Even in embodiments where salt-free reactible hydroxylamine solution is used as the starting material, impurities such as phthalic acid and water may exist on the crude NHPI crystals, such that water washing in these embodiments may also be useful. However, advantageously, in embodiments in which salt-free aqueous hydroxylamine solution is contacted with phthalic anhydride, a water wash of the produced NHPI crystals may be omitted, such that the NHPI crystals are passed to their further use (e.g., catalyzing an oxidation reaction, as discussed below) after separation from the slurry, without additional water washing.

In some particularly advantageous embodiments, water washing and separation of solid NHPI crystals are carried out together. For instance, some embodiments include the use of a countercurrent water wash column to simultaneously wash the crude NHPI crystals and separate those crystals from the mother liquor. In some such embodiments, second slurry comprising crude NHPI crystals from processes according to various of the previously described embodiments is fed to the top of a wash column, while water (preferably with temperature within the range from 0° C. to 30° C., more preferably 0° C. to 10° C.) is flowed upward through the column countercurrent to the downward-flowing slurry comprising NHPI crystals in mother liquor. The column may include parallel lamella (e.g., to provide surface area for solids to collect). As the water passes countercurrently to the solids, it removes impurities such as acids, byproduct salts, and the like. The wet solids exit the bottom of the vessel. Vacuum pressure may be applied to the wet solids to assist in further water removal.

Figure 2:
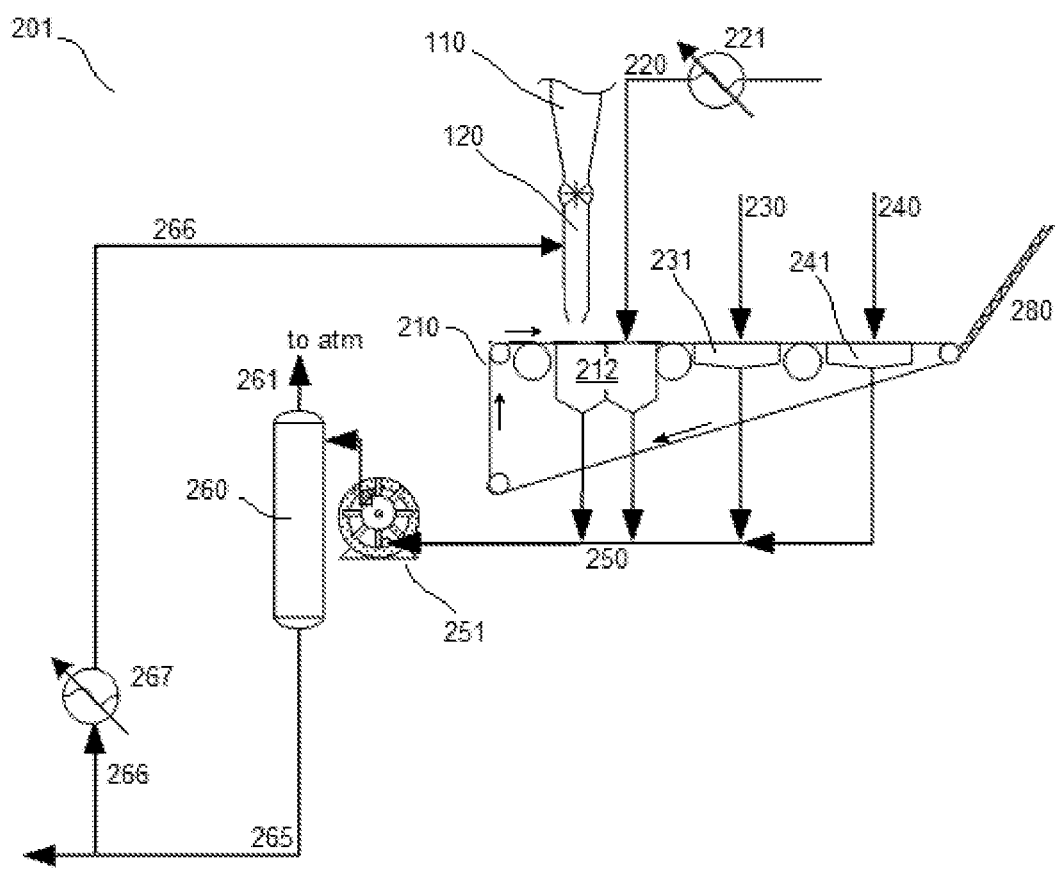
FIG. 2 is a schematic diagram of a process and system for recovering solid cyclic imide in accordance with some embodiments.

In yet other embodiments, water washing and separation of solid NHPI crystals occurs in a wash and vacuum filtration system 201, such as that illustrated in FIG. 2. The second slurry comprising crude NHPI crystals in mother liquor exit the reactor 110 through outlet 120 and are collected upon a filtration belt 210, which moves in the clockwise direction in the system 201 depicted in FIG. 2. The filtration belt 210 conveys the crude solids over one or more mother liquor vacuum devices 212, which aid in removal of the mother liquor from crude solid product. The mother liquor may be collected through the vacuum device (s) 212 as well. Optionally, and as shown in the system 201, a cold water wash may be flowed over the crude solid product via wash conduit 220. The water preferably has temperature between 0° C. and 30° C., more preferably 0° C. to 10° C., such as 3° C. to 6° C. (which temperature may be obtained, e.g., by passing the water wash through a heat exchanger 221). Advantageously, the water wash may be provided to the crude solids over a mother liquor vacuum device 212, such that the vacuum helps remove the water and impurities collected in the wash. The wash in turn is collected through the vacuum device.

The filtration belt 210 may further convey the crude solids to a drying stage, shown in FIG. 2 as comprising flowing steam and then air over the crude solids via steam feed 230 and air feed 240 (although any other inert gas besides air may be used instead, e.g., $N_2$). Further drying vacuum devices 231 and 241, respectively, pull the condensing steam and air, respectively, over and out of the crude solid product. As the steam condenses on the crude solid product, moisture and water-bound impurities may be drawn out from the crystals to aid in further purification. Flowing air subsequently dries the product and cools it after contact with the steam. The solid product NHPI crystals may then be collected and/or conveyed to storage or to an oxidation reaction (e.g., via screw conveyor 280, or via any other suitable means for conveying solids as discussed previously with respect to conveying solid phthalic anhydride).

Two-phase waste product comprising mother liquor (comprising one or more of water, byproduct salts, and byproduct phthalic acid from the reactor 110), water wash (comprising further impurities washed from the solids, such as additional phthalic acid and/or byproduct salts), condensed steam, additional moisture, and air (or other inert gas) are collected in a vacuum conduit 250 in fluid communication with the mother liquor vacuum devices 212 and the drying vacuum devices 231 and 241. A liquid ring vacuum pump 251 or other suitable two-phase pumping device in fluid communication with the vacuum conduit 250 provides the desired work to exert vacuum pressure on the belt 210 via the vacuum devices 212, 231, and 241. Optionally, the pump 251 may also deliver the two-phase waste product to a separation drum 260 or other suitable vapor-liquid separation device, so as to vent air or inert gas via vent conduit 261, while recovering liquid waste water (comprising in various embodiments one or more of byproduct salts, phthalic acid, and water) in wastewater conduit 265. Optionally, as shown in FIG. 2, a portion of the liquid from the wastewater conduit 265 may be split as a recycle stream in recycle conduit 266 and provided to the reactor 110 at a point just upstream of the outlet 120 (e.g., a distance within the range from 0.001 D to 0.05 D upstream of the outlet 120, where D is the height or length of the reactor 110). Advantageously, this recycle stream provides cooling to the second slurry comprising NHPI, which could aid in further precipitation of NHPI product from the second slurry. To further help increase precipitation of solid NHPI product from the second slurry, the recycle stream may be cooled (e.g., by heat exchanger 267).

Waste Water Handling

As noted, solid-liquid separation of the slurry (and, optionally, water washing the recovered NHPI solids) produces a wastewater effluent. The wastewater effluent comprises water, phthalic acid, and possibly also comprises byproduct salts (e.g., salts generated during earlier hydroxylammonium salt reaction with base, in embodiments where such reactions are used to generate the reactable hydroxylamine). In some embodiments, an acid, preferably a strong acid (e.g., sulfuric acid, hydrochloric acid, hydrofluoric acid, etc., preferably sulfuric acid) may be added to the wastewater stream in order to cause precipitation of solid phthalic acid from the wastewater solution. This enables phthalic acid recovery by a further solid/liquid separation (e.g., filtration, vacuum filtration, gravity separation, filter press, clarifier, or the like). The solid phthalic acid may be converted back to phthalic anhydride via dehydration (e.g., using a boronic acid catalyst at temperatures ranging from about 90° C. to 160° C.; or by heating in the absence of catalyst to 220-270° C.). This additional phthalic anhydride may be recycled as additional phthalic anhydride feed to be contacted with the hydroxylamine.

Otherwise, the wastewater may be provided to a water treatment facility, e.g., a biological water treatment facility or the like as would be suitable for removing contaminants (e.g., phthalic acid, byproduct salts) from the water.

Obtained NHPI Crystals

The NHPI crystals obtained through processes according to various embodiments in accordance with those described herein may have advantageous properties for use as an oxidation catalyst in industrial processes. For instance, the NHPI crystals may have particularly desirable dimensions that make them easier to handle in large volumes and/or at large throughput.

In some embodiments, the NHPI crystals have diameter within the range from 5 µm to 50 µm, preferably within the range from 5 µm to 25 µm, such as 7 µm to 15 µm, with ranges from any lower limit to any upper limit also contemplated. The crystals may also or instead have length within the range from 100 µm to 600 µm, preferably 150 µm to 600 µm, such as 200 µm to 525 µm, with ranges from any lower limit to any upper limit also contemplated. Preferably, at least 70 wt %, more preferably at least 80 wt % of the NHPI crystals fall within the foregoing size descriptions.

Characterization of the NHPI crystals may be in accordance with any known, acceptable method of analysis. However, where different analytical methods produce conflicting results, then analytical methods according to the following description shall govern. A Phenom™ G2 pro (available from Phenom-World BV, Eindhoven, The Netherlands) scanning electron microscope (SEM) with light optical camera and multi-segment backscatter detector (BSE), or equivalent equipment, may be used to ascertain the measurement. A 100 µm view with a magnification of 530 and field of view set to 506 µm should be used to measure the dimensions of the NHPI crystals. Each view is achieved by using a ½" slotted head with a carbon adhesive tab. The adhesive tab is pressed into the solid crystal to obtain a sample for analysis. Compressed air is used to dislodge excess material before inserting the slotted head into the SEM, at which time the SEM is zoomed according to the view, magnification, and field of view settings noted above.

Analogous Cyclic Imides

The embodiments described above relating to production of NHPI can also be employed using analogous precursors to form other, similar, cyclic imide catalysts with the same active moiety as NHPI. Specifically, it is believed that NHPI is a radical mediator capable of assisting in radical formation during oxidation reaction of various organic species (in particular, as discussed below, in oxidation of cyclohexylbenzene to cyclohexyl-1-phenyl-1-hydroperoxide). Accordingly, some embodiments provide for the formation of a cyclic imide having the following general formula (I):

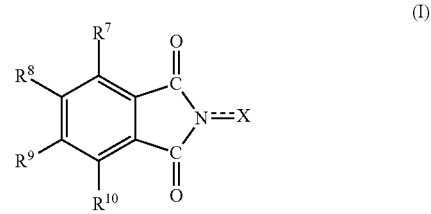

wherein X represents an oxygen atom or a hydroxyl group and each of $R^7$, $R^8$, $R^9$, and $R^{10}$ is independently selected from: (1) H; (2) $C_1$ to $C_{20}$ hydrocarbon groups (preferably linear, branched, or cyclic alkyl groups, or aromatic groups); (3) $SO_3H$; (4) $NH_2$; (5) OH; (6) a halogen (e.g., F, Cl, Br, I);

and (7) NO$_2$, provided that when any 2 adjacent R-groups are both C$_1$ to C$_{20}$ hydrocarbon groups, such adjacent R groups may be joined together to form cyclic (aliphatic or aromatic) rings. Of course, the case in which each of R$^7$, R$^8$, R$^9$, and R$^{10}$ is H, and X is a hydroxyl group, corresponds to NHPI. However, other preferred embodiments include production of a compound in which X is OH, and each of R$^7$, R$^8$, R$^9$, and R$^{10}$ is independently H or a linear, cyclic, or aromatic alkyl group having 1 to 20, more preferably 1 to 6, carbon atoms. More preferably, each of R$^7$, R$^8$, R$^9$, and R$^{10}$ is independently selected from one of: (i) H and (ii) linear or branched alkyl groups having 1 to 5, more preferably 1 to 3, carbon atoms.

Accordingly, instead of phthalic anhydride, analogous carboxylic acid anhydrides corresponding to the above general formula (I) may be reacted with hydroxylamine in embodiments in accordance with the various embodiments described herein. That is, embodiments described with reference to "phthalic anhydride" may instead be practiced using, instead of or in addition to the phthalic anhydride, a carboxylic acid anhydride according to the general formula (II):

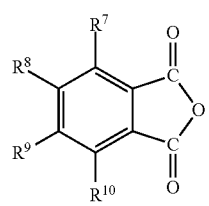

(II)

wherein each of R$^7$, R$^8$, R$^9$, and R$^{10}$ is defined as above with reference to the general formula (I), with the same preferences noted for carboxylic acid anhydrides of various embodiments.

As will be apparent, the carboxylic acid anhydride of general formula (II) will undergo analogous reaction with hydroxylamine to form an intermediate hydroxamic acid, in a similar manner as seen with phthalic anhydride's reaction with hydroxylamine to form intermediate NHPA, which is in turn converted to NHPI by heating. The solid intermediate hydroxamic acids of various embodiments are in accordance with the following general formula (III):

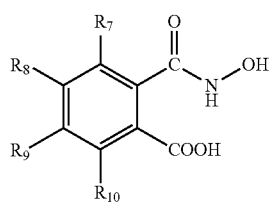

(III)

wherein each of R$^7$, R$^8$, R$^9$, and R$^{10}$ is defined as above with reference to the general formula (I), with the same preferences noted for hydroxamic acids of various embodiments.

Likewise, the carboxylic acid anhydride of general formula (II) may also undergo side reactions to form dicarboxylic acid byproducts having analogous structural formula to the byproduct phthalic acid generated from phthalic anhydride, as shown in general formula (IV):

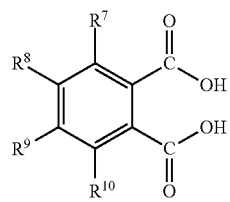

(IV)

wherein each of R$^7$, R$^8$, R$^9$, and R$^{10}$ is defined as above with reference to the general formula (I), with the same preferences noted for dicarboxylic acid byproducts of various embodiments.

Use of the Cyclic Imide as an Oxidation Catalyst

The processes and systems for making cyclic imide catalysts disclosed herein can be used in various oxidation processes. Of particular interest is the oxidation of cyclohexylbenzene to cyclohexyl-1-phenyl-1-hydroperoxide (also referred to herein as cyclohexylbenzene hydroperoxide). This reaction is of particular interest when integrated into a process to produce cyclohexanone and/or phenol from benzene via hydroalkylation, as described in, e.g., WIPO Publication Nos. WO 2014/137623 and WO 2016/053583.

Thus, processes of some embodiments may include obtaining cyclohexylbenzene, obtaining a cyclic imide oxidation catalyst (e.g., by any of the methods described herein), and contacting the cyclohexylbenzene and the cyclic imide oxidation catalyst so as to produce an oxidation effluent comprising cyclohexylbenzene-hydroperoxide. Such processes may further include contacting the oxidation effluent with a cleavage catalyst so as to obtain a cleavage effluent comprising phenol and cyclohexanone.

Supply of Cyclohexylbenzene

The cyclohexylbenzene contacted with the cyclic imide oxidation catalyst can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction (3) to produce cyclohexylbenzene (CHB):

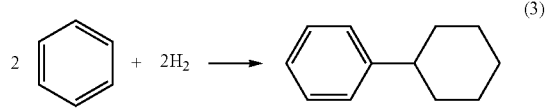

(3)

Alternatively, cyclohexylbenzene can be produced by direct alkylation of benzene with cyclohexene in the presence of a solid-acid catalyst such as molecular sieves in the MCM-22 family according to the following Reaction (4):

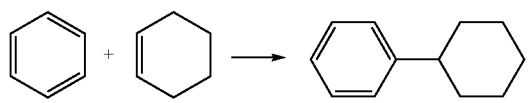

(4)

Side reactions may occur in Reaction (3) or Reaction (4) to produce some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants Thus, typically, after the reaction, the hydroalkylation reaction product mixture is separated by distillation to obtain a $C_6$ fraction containing benzene, cyclohexane, a $C_{12}$ fraction containing cyclohexylbenzene and methylcyclopentylbenzene, and a heavies fraction containing, e.g., $C_{18}$s such as DiCHBs and $C_{24}$s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step. Depending on the quantity of the heavies fraction, it may be desirable to either (a) transalkylate the $C_{18}$s such as DiCHB and $C_{24}$s such as TriCHB with additional benzene or (b) dealkylate the $C_{18}$s and $C_{24}$s to maximize the production of the desired monoalkylated species.

Details of feed materials, catalyst used, reaction conditions, and reaction product properties of benzene hydroalkylation, and transalkylation and dealkylation, can be found in, e.g., Paragraphs [0031], [0032]-[0034], and [0036]-[0048] of WIPO Publication No. WO 2016/053583, which description is incorporated by reference herein.

Oxidation of Cyclohexylbenzene

The cyclohexylbenzene (e.g., obtained per the processes described above) is contacted with the cyclic imide oxidation catalyst (e.g., NHPI) obtained from processes consistent with any of those embodiment described herein, whereupon at least a portion of the cyclohexylbenzene is converted to cyclohexyl-1-phenyl-1-hydroperoxide, the desired hydroperoxide, according to the following Reaction (5):

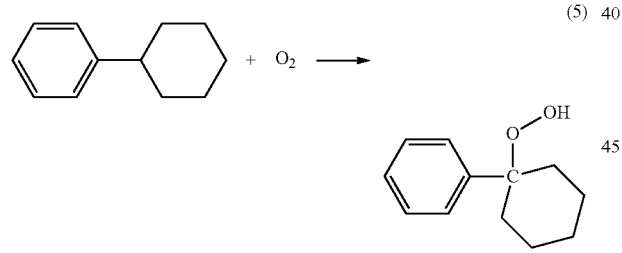

(5)

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

In exemplary processes, the oxidation may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor to effect the oxidation.

Details of the feed material, reaction conditions, reactors used, product mixture composition and treatment, and the like, of the oxidation can be found in, e.g., Paragraphs [0049]-[0071] of WIPO Publication No. WO 2016/053583, which description is incorporated by reference herein.

Cleavage Reaction and Obtaining Phenol and/or Cyclohexanone

At least a portion of the cyclohexyl-1-phenyl-1-hydroperoxide may in some embodiments be subsequently contacted with an acid catalyst so as to decompose at least a portion of the cyclohexyl-1-phenyl-1-hydroperoxide to cyclohexanone and phenol according to the following desired Reaction (6):

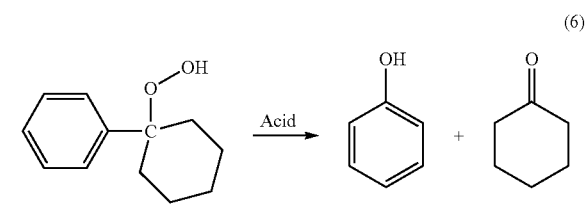 [SMILES: OOC1(c2ccccc2)CCCCC1 ; Oc1ccccc1 ; O=C1CCCCC1]

(6)

The cleavage product mixture may comprise the acid catalyst, phenol, cyclohexanone, cyclohexylbenzene, and contaminants.

The acid catalyst preferably is at least partially soluble in the cleavage reaction mixture, is stable at a temperature of at least 185° C., and has a lower volatility (higher normal boiling point) than cyclohexylbenzene.

Feed composition, reaction conditions, catalyst used, product mixture composition and treatment thereof, and the like, of this cleavage step can be found in, e.g., Paragraphs [0072]-[0084] of WIPO Publication No. WO 2016/053583, which description is incorporated by reference herein.

Further separation and/or processing of the cleavage product mixture, e.g., to obtain phenol and/or cyclohexanone products, may take place as described in Paragraphs [0085]-[00127] of WIPO Publication No. WO 2016/053583, which description is incorporated by reference herein.

EXAMPLES

Experimental Set-Up

Figure 3:
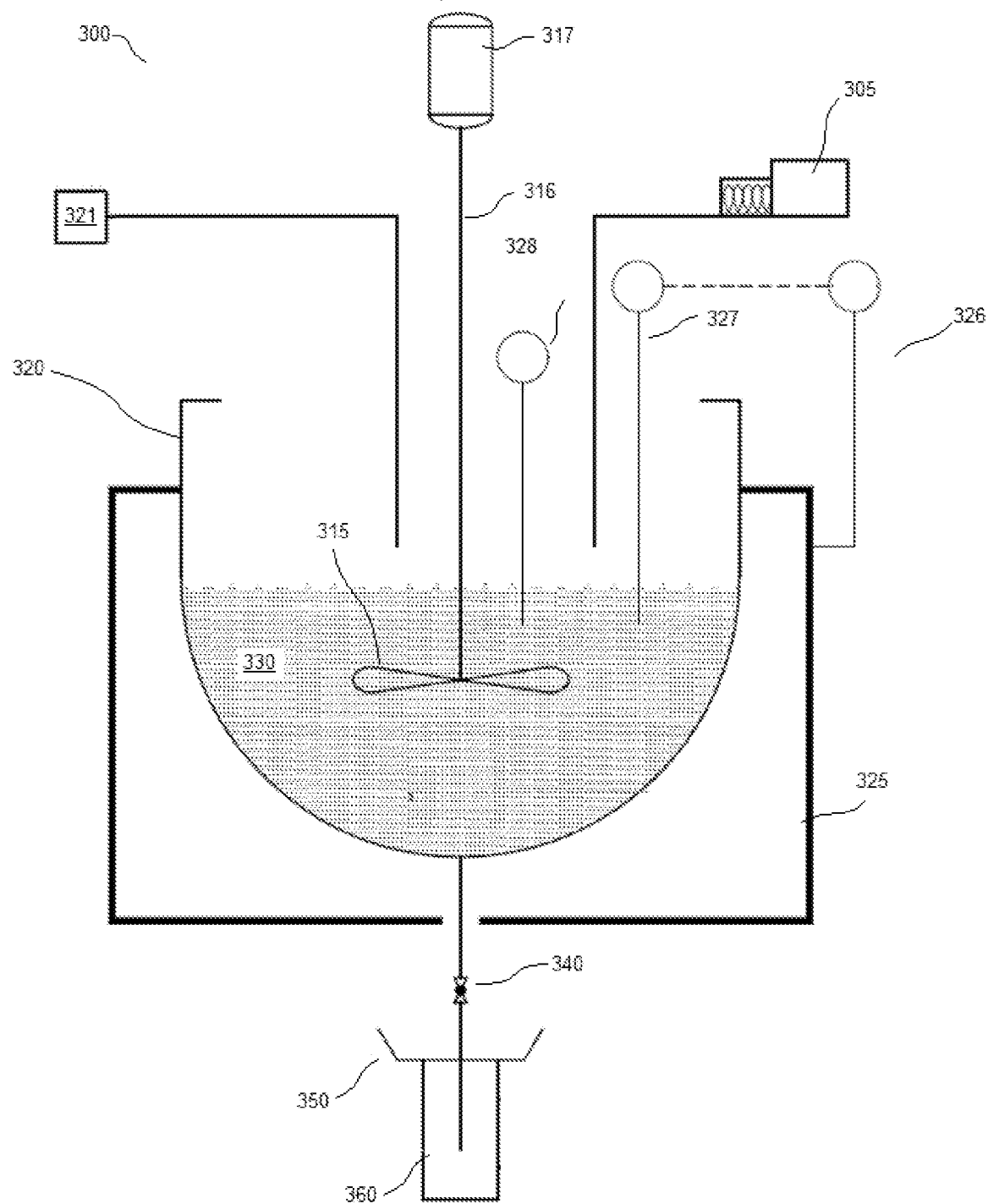
FIG. 3 is a schematic diagram of a semi-batch reactor system used in carrying out reactions in accordance with the description of the Examples.

A scaled-down reactor for generating NHPI in a semi-batch process was set up according to FIG. 3. The equipment 300 included a two-liter glass reactor vessel 320 equipped with a triple propeller 315 on a glass stirring rod 316 coupled to a digital stirring motor 317. One syringe pump 321 was used for continuous addition of liquid base solution (NaOH in water or $NH_3$ in water, as applicable in each experiment described below), and solid doser 305 provided continuous addition of phthalic anhydride crystals into the reactor vessel 320. A heating mantle 325 was utilized to maintain automated temperature control in the reactor via a heating controller 326 electrically connected to the heating mantle 325 and a thermocouple 327 disposed in the reaction medium 330 within the reactor vessel 320. A pH probe 328 was also disposed in the reaction medium 330 to monitor pH. The bottom of the reaction vessel 320 was equipped with a two-way valve 340 for slurry drainage through a Buechner funnel 350 disposed over a two-liter Erlenmeyer flask 360 maintained under vacuum pressure for collection of crude solids.

Analytical Methods

Detailed characterization of the NHPI production samples was performed by high pressure liquid chromatography (HPLC), carbon nuclear magnetic resonance spectroscopy ($^{13}$C-NMR), proton nuclear magnetic resonance spectroscopy ($^1$H-NMR), ion chromatography (IC), inductively coupled plasma elemental analysis (ICP), moisture determination by coulometric Karl Fischer titration (KF), pH tests, temperature measurements, and crystal dimensions by scanning electron microscopy (SEM).

The HPLC used was an Agilent 1260 in reversed phase; the column was a Phenomenex Kinetex.2.6u Phenyl-Hexyl 100A, 75 mm×2.1 mm, part number 00C-4495-AN. Injection volume was 0.3 µL, column temperature was 30° C., and dual solvents (Solvent A=0.1% Formic Acid, 2.5% MeOH in H$_2$O; and Solvent B=Methanol) were used with the following Gradient in Table 1:

TABLE 1

HPLC program

| Time (min) | Solvent A (%) | Solvent B (%) | Flow rate mL/min |
|---|---|---|---|
| 0 | 85 | 15 | 0.3 |
| 8 | 85 | 15 | 0.3 |
| 12 | 5 | 95 | 0.3 |
| 17 | 5 | 95 | 0.3 |
| 20 | 85 | 15 | 0.3 |
| 25 | 85 | 15 | 0.3 |

Elution times were as follows: NHPA at 1.1 min, phthalamic acid at 1.3 min, phthalic acid at 2.8 min, phenol at 3.2 min, NHPI at 3.6 min, phthalimide at 4.9 min, and phthalic anhydride at 13.1 min. The detector was an Ultra-Violet source with diode array detector (DAD) signals collected at 210, 225 (for quantitative data), and 254 nm. Samples for the HPLC were prepared in a tarred vial and ethanol was added as a diluent (approx. 2 g of ethanol with 0.002 g of NHPI sample).

Example 1: Hydroxylammonium Salt Reaction with NaOH

Multiple test runs (11) for hydroxylammonium salt reaction with sodium hydroxide, followed by reaction between hydroxylamine and phthalic anhydride, were carried out according to the following procedures (with typical observations also reported).

Water (499 g, 21° C.) was added to the reactor vessel 320, followed by addition of 158 g of hydroxylammonium sulfate ((NH$_3$OH)$_2$SO$_4$) under stirring. The liquid reactor content was stirred at 21° C. until the hydroxylammonium sulfate was fully dissolved. Then, over the course of 30 minutes, 154 g of a 50 wt % NaOH solution (aqueous) was continuously added to the hydroxylammonium salt solution. Temperature of the reactor content was controlled during addition of the NaOH solution such that maximum temperature did not exceed 37° C.; stirring speed was set to 300 rpm. Stirring continued for 10 minutes after completion of the base addition, after which time pH of the reactor content was approximately 9.0 and temperature was 35° C.

Solid phthalic anhydride (256 g) was then added to the reactor content at a rate of 5 g/min under stirring (300 rpm). Temperature rose during the addition, and following this addition, heat was applied to the reactor 320 via the external heating mantle 325 such that temperature of the reactor content rose to 67° C. at a rate of 1.2° C./min Water was then added (575 g, 21° C. water temperature).

By the time reactor content temperature had reached 67° C., formation of a slurry or butter-like paste was typically observed in the reactor content, due to formation and precipitation of solids. The added 575 g water made the reactor content easier to stir. Upon completion of water addition, reactor content temperature was about 45° C.

The reactor content was then heated to 90° C. at 1.2° C./min, and stirred for 15 minutes holding at 90° C. At first, stirring of the 90° C. reactor content was not difficult; however, as NHPI crystals formed during the heating and stirring (indicated by the transition of the reactor content to a second slurry), stirring became more difficult. After 15 minutes of stirring, the reactor content pH is approximately 3.6.

The valve on the bottom of the reactor was then opened, and the 90° C. slurry drained into the settling vessel. The slurry in the settling vessel was allowed to cool to 21° C. without stirring over the course of 20 hours. The slurry was then poured into the Buechner/Erlenmeyer/Vacuum filtration system to separate the mother liquor from the crude NHPI crystals. The crude crystals were vacuum filtered for 90 minutes, by which time liquid down flow had ceased. The pH of the collected mother liquor was 4.2. The crude crystals were transferred to a vacuum oven (temperature set to 75° C.), and left in the oven for about 6 hours (at which time no further weight loss was recorded). Recorded weight of recovered NHPI crystals was 215 g.

100 g of the recovered NHPI crystals were removed and further washed with ice water (4 250 mL washes) to remove any water soluble impurities (e.g., sodium sulfate), followed by another 30 minutes of vacuum filtration of the crystals. Further heating in the vacuum oven at 75° C. followed for a duration of 20 hours, after which the product was analyzed for purity according to the analytical methods noted previously.

Example 2: Hydroxylammonium Salt Reaction with NH$_3$

Two test runs for hydroxylammonium salt reaction with ammonia, followed by reaction between hydroxylamine and phthalic anhydride, were carried out according to the following procedures (with typical observations also reported).

Water (534 g, 21° C.) was added to the reactor, followed by 160 g of hydroxylammonium sulfate ((NH$_3$OH)$_2$SO$_4$) under stirring. The liquid reactor content was stirred at 21° C. until the hydroxylammonium sulfate was fully dissolved. Then, over the course of 15 minutes, 127 g of a 29 wt % NH$_3$ solution (aqueous) was added to the hydroxylammonium salt solution. Temperature of the reactor content was controlled during addition of the NH$_3$ solution such that maximum temperature did not exceed 25° C.; stirring speed was set to 300 rpm. Stirring continued for 1 minute after completion of the base addition, after which time pH of the reactor content was approximately 9.0 and temperature was 25° C. Times for addition and stirring were substantially lower for NH$_3$ reaction with hydroxylammonium salt as compared to NaOH reaction with hydroxylammonium salt, due to the lower exotherm observed for the NH$_3$-based reaction; further, it was very easy to maintain the temperature of the reactor contents at 25° C. instead of 35° C. (as was the case with NaOH-based reaction).

Solid phthalic anhydride (259 g) was then added to the reactor content at a rate of 8 g/min under stirring (300 rpm); again, a lower exotherm in the NH$_3$-based route as compared to NaOH-based route allowed shorter time for this step as compared to the NaOH-based route. Temperature rose during the addition, and following this addition, heat was applied to the reactor via the external heating mantle such that temperature of the reactor content rose to 67° C. at a rate of 1.0° C./min. Water was then added (542 g, 21° C. water temperature).

By the time reactor content temperature had reached 67° C., formation of a slurry or butter-like paste was typically observed in the reactor content; the 542 g of added water made the reactor content easier to stir. Upon completion of water addition, reactor content temperature was about 51° C.

The reactor content was then heated to 90° C. at 1.2° C./min, and stirred for 15 minutes holding at 90° C. At first, stirring of the 90° C. reactor content was not difficult; however, during the course of stirring, NHPI crystals form, as indicated by the transition of the reactor content to a second slurry forms that makes stirring more difficult. After 15 minutes of stirring, the reactor content pH was approximately 4.3.

The valve on the bottom of the reactor was then opened, and the 90° C. slurry drained into the settling vessel. The slurry in the settling vessel was allowed to cool to 21° C. without stirring over the course of 20 hours. The slurry was then poured into the Buechner/Erlenmeyer/Vacuum filtration system to separate the mother liquor from the crude NHPI crystals. The crude crystals were vacuum filtered for 90 minutes, by which time liquid down flow had ceased. The pH of the collected mother liquor was 4.6. The crude crystals were transferred to a vacuum oven (temperature set to 75° C.), and left in the oven for about 10 hours (at which time no further weight loss was recorded). Recorded weight of recovered NHPI crystals was 215 g.

100 g of the recovered NHPI crystals were washed with ice water (4 250 mL washes) to remove any water insoluble impurities (e.g., sodium sulfate), followed by another 30 minutes of vacuum filtration of the crystals. Further heating in the vacuum oven at 75° C. followed for a duration of 20 hours, after which the product was analyzed for purity according to the analytical methods noted previously.

Example 3: Salt-Free Hydroxylamine Solution as Starting Reagent

One test run for salt-free hydroxylamine reaction with phthalic anhydride was carried out according to the following procedures (with typical observations also reported).

139.4 g of salt-free hydroxylamine aqueous solution (50 wt % in water) were added to the reactor, along with 396 g of water (21° C.) under stirring, resulting in a salt-free 13% hydroxylamine aqueous solution. Stirring continued for 10 minutes to ensure proper mixing, after which time pH of the reactor content was approximately 8.3 and temperature was 21° C.

Solid phthalic anhydride (281 g) was then added to the reactor content in the reactor at a rate of 9 g/min under stirring (300 rpm). Temperature rose during the addition, and following this addition, heat was applied to the reactor via the external heating mantle such that temperature of the reactor content rose to 67° C. at a rate of 1.1° C./min. Water was then added (798 g, 21° C. water temperature).

By the time reactor content temperature had reached 67° C., formation of a butter-like paste or slurry was typically observed in the reactor content; the 798 g of added water made the reactor content easier to stir. Upon completion of water addition, temperature of the reactor content was about 45° C.

The reactor content was then heated to 90° C. at 1.2° C./min, and stirred for 15 minutes holding at 90° C. At first, stirring of the 90° C. reactor content was not difficult; however, during the course of stirring, NHPI crystals formed, as indicated by the transition of the reactor content to a second slurry forms that made stirring more difficult. After 15 minutes of stirring, the reactor content pH was 3.7.

The valve on the bottom of the reactor was then opened, and the 90° C. slurry drained into the settling vessel. The slurry in the settling vessel was allowed to cool to 21° C. without stirring over the course of 20 hours. The slurry was then poured into the Buechner/Erlenmeyer/Vacuum filtration system to separate the mother liquor from the crude NHPI crystals. The crude crystals were vacuum filtered for 90 minutes, by which time liquid down flow had ceased. The pH of the collected mother liquor was 3.8. The crude crystals were transferred to a vacuum oven (temperature set to 75° C.), and left in the oven for about 14 hours (at which time no further weight loss was recorded). Recorded weight of recovered crude NHPI crystals was 222 g. The crystals were then analyzed for product purity according to the analytical methods noted previously, without water washing.

Analysis and Comparison of Examples 1-3

Table 2 below summarizes the crude product measurements for each Example experiment. Table 3 below summarizes the measurements on recovered solid product from Examples 1 and 2 following water wash (again, no water wash was undertaken for Example 3 to demonstrate the relatively high purity obtained without water washing in such processes).

TABLE 2

| Crude Solid Analysis | | | |
|---|---|---|---|
| | Example | | |
| | 1 | 2 | 3 |
| Weight of mother liquor (ML) after Buechner (g) | 1290.2 | 1271.2 | 1255.8 |
| pH of ML | 4.2 | 4.6 | 3.9 |
| Weight of solids after Buechner, before oven drying (g) | 256.5 | 269.5 | 258.6 |
| Time of oven drying @ 75° C. under vacuum (h) | 5.9 | 16.0 | 14.3 |
| Nitrogen flow rate into oven (SCFH) | 0.0 | 2.0 | 2.0 |
| Dry product weight (g) | 215.3 | 213.4 | 221.9 |
| Yield (%) on basis of phthalic anhydride (PAN) reactant | 72.8 | 69.6 | 69.7 |
| Yield (%) on basis of HAS precursor to hydroxylamine reactant | 65.3 | 62.5 | n/a |
| Yield (%) on basis of hydroxylamine reactant | 65.4 | 62.5 | 62.6 |
| Phthalic Anhydride conversion to products + byproducts | 73.6 | 70.4 | 70.1 |
| Sulfate content by IC (wppm) | 19006 | 27921 | 34 |
| Chloride by IC (wppm) | 1449 | 893 | 965 |
| $Na^+$ or $NH_4^+$ calculated or by ICP (ppm) | 10096 | 10940 | 504 |
| Water content by KF (wt %) | 0.53 | 1.67 | 1.88 |
| Organic impurities by NMR (%) | 1.30 | 1.50 | 1.00 |
| pH of 1000 ppm dry product in DI water | 4.33 | 4.5 | 4.4 |
| ML (g) - max (calculated) | 1437 | 1424 | 1400 |
| ML N content (ppm) - max (calculated) | 6501 | 28484 | 7907 |
| ML Na content - max (calculated) | 30732 | 0 | 0 |
| ML $SO_4$ content - max (calculated) | 64275 | 65690 | 0 |
| ML C content - max (calculated) | 31652 | 36164 | 39816 |
| Purity of crude crystals (NHPI, wt %) | 95.1 | 93.0 | 97.0 |

TABLE 3

Solid Analysis After Water Wash of 100 g of Crystals

| | Example 1 | Example 2 |
|---|---|---|
| water per wash (g) | 250.0 | 250.0 |
| # washing steps | 4.0 | 4.0 |
| Temp of water (° C.) | 1.5 | 5.2 |
| Time of last Buechner filtration under vacuum (min) | 30.0 | 15.0 |
| NHPI before wash (g) | 100.1 | 150.1 |
| Time of product drying @ 75° C. under vacuum (h) | 21.0 | 24.8 |
| Final dry product wt (g) | 93.6 | 142.2 |
| Yield (%) on basis of PAN reactant | 69.8 | 69.1 |
| Yield (%) on basis of HAS precursor to HA reactant | 62.6 | 62.0 |
| Sulfate content by IC (wppm) | 19 | 159.0 |
| Chloride content by IC (wppm) | 1606.1 | 810.0 |
| Sodium content by ICP (ppm) | 373.5 | 471.8 |
| Water content by KF (wt %) | 0.28 | 1.7 |
| Organic impurities by NMR (wt %) | 0.0 | 0.0 |
| pH of 1000 ppm dry NHPI in DI water | 4.27 | 4.7 |
| Purity (NHPI, wt %) | 99.5 | 98.1 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. The contents of all references cited herein are incorporated by reference in their entirety.

The invention claimed is:

1. A process comprising:
   (a) contacting a hydroxylamine solution with a cyclic carboxylic acid anhydride so as to form a reaction medium having initial temperature $T_i$ of less than 65° C.;
   (b) raising the reaction medium temperature to a transition temperature $T_t$ within the range from 65° C. to less than 75° C., thereby forming a first slurry comprising solid intermediate hydroxamic acid within the reaction medium;
   (c) further heating the reaction medium to a final temperature $T_f$ within the range from 75° C. to 200° C., thereby converting at least a portion of the solid intermediate hydroxamic acid to solid cyclic imide, such that the reaction medium comprises a second slurry comprising the solid cyclic imide;
   wherein the cyclic carboxylic acid anhydride has the general formula (II)

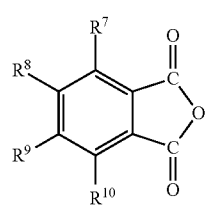

and further wherein the cyclic imide has the general formula (I)

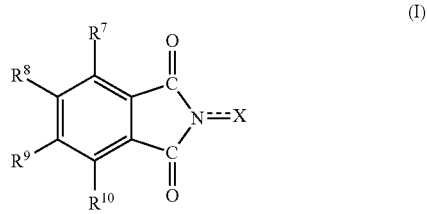

where, in each formula (I) and (II), X is an oxygen atom or a hydroxyl group, and further wherein each of $R^7$, $R^8$, $R^9$, and $R^{10}$ is independently selected from: (1) H; (2) $C_1$ to $C_{20}$ linear, cyclic, or aromatic hydrocarbon groups; (3) $SO_3H$; (4) $NH_2$; (5) OH; (6) a halogen; and (7) $NO_2$;

wherein the process comprises continuously feeding the hydroxylamine solution and carboxylic acid anhydride to a continuous flow reactor via one or more feed inlets, so as to establish the reaction medium flowing continuously in a downstream direction within the continuous flow reactor; at a second location along the continuous flow reactor that is downstream of the one or more feed inlets, feeding steam or water into the reaction medium; at a third location along the continuous flow reactor that is downstream of the second location, feeding additional steam or additional water into the reaction medium; agitating the reaction medium within the continuous flow reactor between the second and third locations; and recovering a reaction product comprising solid cyclic imide from the reaction medium; and wherein, the continuous flow reactor is in fluid communication with (i) a first steam conduit and (ii) a second steam conduit downstream of the first steam conduit, wherein (b) raising the reaction medium temperature to the transition temperature $T_t$ comprises adding steam to the reaction medium through the first steam conduit, and wherein (c) further heating the reaction medium to the final temperature $T_f$ comprises adding additional steam to the reaction medium through the second steam conduit.

2. The process of claim 1, wherein each of $R^7$, $R^8$, $R^9$, and $R^{10}$ is independently selected from one of: (i) H and (ii) linear or branched alkyl groups having 1 to 5 carbon atoms.

3. The process of claim 2, wherein the carboxylic acid anhydride is phthalic anhydride, the intermediate hydroxamic acid is N-hydroxyphthalamic acid (NHPA), and the cyclic imide is N-hydroxyphthalimide (NHPI).

4. The process of claim 1, wherein the temperature of the reaction medium is raised from the initial temperature $T_i$ to the transition temperature $T_t$ at a rate within the range from 0.01 to 500° C./min.

5. The process of claim 1, further comprising monitoring the temperature of the reaction medium at a first location and, based at least in part upon the temperature at the first location, controlling one or both of (i) reaction medium flow rate in the continuous flow reactor and (ii) flow rate of the steam through the first conduit in order to raise the reaction medium temperature to the transition temperature $T_t$.

6. The process of claim 5, wherein the controlling results in raising the reaction medium temperature from the initial temperature $T_i$ to the transition temperature $T_t$ at a rate within the range from 0.01 to 500° C./min.

7. The process of claim 1, further comprising monitoring the temperature of the reaction medium at a second location and, based at least in part upon the temperature at the second location, controlling one or both of (i) reaction medium flow rate in the continuous flow reactor and (ii) flow rate of the additional steam through the second steam conduit in order to raise the reaction medium temperature to the final temperature $T_f$.

8. The process of claim 1, wherein the hydroxylamine solution comprises (a) 30-70 wt % hydroxylamine, (b) water, and (c) less than 1 wt % of compounds other than hydroxylamine and water.

9. The process of claim 1, wherein the hydroxylamine solution is formed by a process comprising:
   (a-1) contacting a hydroxylammonium salt with an aqueous base to form at least a portion of said hydroxylamine solution.

10. The process of claim 9, wherein the hydroxylammonium salt is hydroxylammonium sulfate.

11. The process of claim 9, wherein the aqueous base is selected from the group consisting of sodium hydroxide and ammonia.

12. The process of claim 1, wherein the solid cyclic imide comprises NHPI crystals having diameter within the range from 5 µm to 50 µm, and length within the range from 200 µm to 525 µm.

13. The process of claim 1, further comprising providing at least a portion of the solid cyclic imide to an oxidation reaction.

14. The process of claim 1, further comprising contacting at least a portion of the solid cyclic imide with cyclohexylbenzene and an oxygen-containing gas so as to obtain cyclohexyl-1-phenyl-1-hydroperoxide.

15. A process comprising:
   (a) contacting a hydroxylamine solution with a cyclic carboxylic acid anhydride so as to form a reaction medium having initial temperature $T_i$ of less than 65° C.;
   (b) raising the reaction medium temperature to a transition temperature $T_t$ within the range from 65° C. to less than 75° C., thereby forming a first slurry comprising solid intermediate hydroxamic acid within the reaction medium;
   (c) further heating the reaction medium to a final temperature $T_f$ within the range from 75° C. to 200° C., thereby converting at least a portion of the solid intermediate hydroxamic acid to solid cyclic imide, such that the reaction medium comprises a second slurry comprising the solid cyclic imide;
   wherein the cyclic carboxylic acid anhydride has the general formula (II)

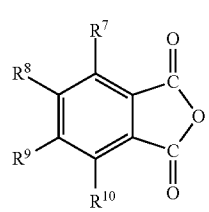

and further wherein the cyclic imide has the general formula (I)

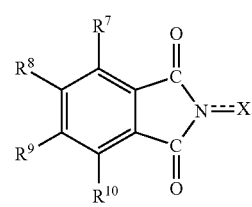

where, in each formula (I) and (II), X is an oxygen atom or a hydroxyl group, and further wherein each of $R^7$, $R^8$, $R^9$, and $R^{10}$ is independently selected from: (1) H; (2) $C_1$ to $C_{20}$ linear, cyclic, or aromatic hydrocarbon groups; (3) $SO_3H$; (4) $NH_2$; (5) OH; (6) a halogen; and (7) $NO_2$;

wherein the process comprises continuously feeding the hydroxylamine solution and carboxylic acid anhydride to a continuous flow reactor via one or more feed inlets, so as to establish the reaction medium flowing continuously in a downstream direction within the continuous flow reactor; at a second location along the continuous flow reactor that is downstream of the one or more feed inlets, feeding steam or water into the reaction medium; at a third location along the continuous flow reactor that is downstream of the second location, feeding additional steam or additional water into the reaction medium; agitating the reaction medium within the continuous flow reactor between the second and third locations; and recovering a reaction product comprising solid cyclic imide from the reaction medium;

(d) obtaining from the second slurry (i) a plurality of solid cyclic imide crystals and (ii) a wastewater effluent comprising a dicarboxylic acid byproduct having the general formula (III):

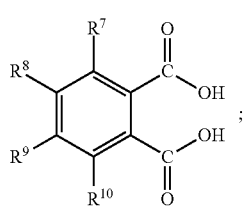

wherein obtaining the plurality of solid cyclic imide crystals and the wastewater effluent comprises:
(d-1) collecting at least a portion of the second slurry comprising solid cyclic imide crystals and mother liquor on a filtration belt;
(d-2) passing the filtration belt having solid cyclic imide crystals disposed thereon over one or more vacuum devices;
(d-3) contacting the solid cyclic imide crystals disposed on the filter belt with wash water having temperature within the range from 0° C. to 30° C.;
(d-4) contacting the solid cyclic imide crystals disposed on the filter belt with drying steam and then with an inert gas, such that at least a portion of the drying steam condenses on the solid cyclic imide crystals;

(d-5) after carrying out (d-1) through (d-4), collecting the solid cyclic imide crystals in a solid conveyor;
(d-6) collecting at least a portion of the mother liquor;
(d-7) collecting at least a portion of each of the wash water, condensed drying steam, and inert gas after each contacts the solid cyclic imide crystals; and
(d-8) combining said portions of each of the mother liquor, wash water, condensed drying steam, and inert gas to form the wastewater effluent.

16. The process of claim 15, further comprising:
(e) contacting the wastewater effluent with a strong acid, thereby precipitating solid dicarboxylic acid byproduct from the wastewater effluent;
recovering the precipitated dicarboxylic acid byproduct from the wastewater effluent by solid/liquid separation; and
(g) dehydrating at least a portion of the recovered dicarboxylic acid byproduct so as to form additional cyclic carboxylic acid anhydride.

17. The process of claim 16, wherein the additional cyclic carboxylic acid anhydride constitutes at least part of the cyclic carboxylic acid anhydride contacted with the hydroxylamine solution in (a).

18. The process of claim 15, wherein the dicarboxylic acid byproduct comprises phthalic acid.

* * * * *